US010041886B2

(12) United States Patent
Xiong et al.

(10) Patent No.: US 10,041,886 B2
(45) Date of Patent: Aug. 7, 2018

(54) MONOLAYER OF NANORODS ON A SUBSTRATE AND METHOD OF FORMING THE SAME

(71) Applicant: NANYANG TECHNOLOGICAL UNIVERSITY, Singapore (SG)

(72) Inventors: Qihua Xiong, Singapore (SG); Bo Peng, Singapore (SG)

(73) Assignee: Nanyang Technological University, Singapore (SG)

( * ) Notice: Subject to any disclaimer, the term of this patent is extended or adjusted under 35 U.S.C. 154(b) by 349 days.

(21) Appl. No.: 14/773,195

(22) PCT Filed: Mar. 5, 2014

(86) PCT No.: PCT/SG2014/000107
§ 371 (c)(1),
(2) Date: Sep. 4, 2015

(87) PCT Pub. No.: WO2014/137292
PCT Pub. Date: Sep. 12, 2014

(65) Prior Publication Data
US 2016/0018335 A1    Jan. 21, 2016

Related U.S. Application Data

(60) Provisional application No. 61/773,617, filed on Mar. 6, 2013.

(51) Int. Cl.
| | | |
|---|---|---|
| *B05D 3/04* | (2006.01) | |
| *B05D 3/06* | (2006.01) | |
| *G01N 21/65* | (2006.01) | |
| *B81C 1/00* | (2006.01) | |
| *B82Y 40/00* | (2011.01) | |
| *B82Y 30/00* | (2011.01) | |
| *B82Y 20/00* | (2011.01) | |

(52) U.S. Cl.
CPC ......... *G01N 21/658* (2013.01); *B05D 3/0486* (2013.01); *B05D 3/066* (2013.01); *B81C 1/00111* (2013.01); *B81C 2201/0149* (2013.01); *B82Y 20/00* (2013.01); *B82Y 30/00* (2013.01); *B82Y 40/00* (2013.01)

(58) Field of Classification Search
CPC ... B05D 3/0486; B05D 3/066; B81C 1/00111; B81C 2201/0149; G01N 21/658
USPC .... 427/212, 214, 241, 372.2, 377, 485, 553, 427/601
See application file for complete search history.

(56) References Cited

FOREIGN PATENT DOCUMENTS

| CN | 101011745 A | 8/2007 |
|---|---|---|
| CN | 101818346 A | 9/2010 |
| CN | 102728831 A | 10/2012 |

OTHER PUBLICATIONS

Bigioni et al. Kinetically driven self assembly of highly ordered nanoparticle monolayers. Nature Materials vol. 5 (2006) (Year: 2006).*
Novotny et al. Gold nanorod arrays: optical properties. Nanocon 2012 (Year: 2012).*
Ming et al. Ordered gold nanostructure assemblies formed by droplet evaporation. Angewandte Chemie vol. 47, p. 9685-9690 (2008) (Year: 2008).*
*2008 Chinese milk scandal—Wikipedia, the free encyclopedia* [online][retrieved Oct. 15, 2015]. Retrieved from the Internet: <URL: http://En.Wikipedia.Org/Wiki/2008_Chinese_Milk_Scandal>. (Oct. 9, 2015) 35 pages.
*2011 Taiwan food scandal—Wikipedia, the free encyclopedia* [online][retrieved Oct. 15, 2015]. Retrieved from the Internet: <URL: http://En.Wikipedia.Org/Wiki/2011_Taiwan_Food_Scandal>. (Jul. 27, 2015) 4 pages.
Ai, K. et al., *Hydrogen-Bonding Recognition-Induced Color Change of Gold Nanoparticles for Visual Detection of Melamine in Raw Milk and Infant Formula*, Journal of American Chemical Society, vol. 131 (2009) 9496-9497.
Alkilany, A. M. et al., *Gold Nanorods as Nanoadmicelles: 1-Naphthol Partitioning into a Nanorod-Bound Surfactant Bilayer*, Langmuir, vol. 24 (2008) 10235-10239.
Alvarez-Peubla, R. A. et al., *Gold Nanorods 3d-Supercrystals as Surface Enhanced Raman Scattering Spectroscopy Substrates for the Rapid Detection of Scrambled Prions*, Proc. Natl. Acad. Sci. (2011) 11 pages.
Alvarez-Puebla, R. A. et al., *Surface-Enhanced Raman Scattering for Ultrasensitive Chemical Analysis of 1 and 2-Naphthalenethiols*,Analyst , vol. 129, (2004) 1251-1256.
Anker, J. N. et al., *Biosensing with Plasmonic Nanosensors*, Nature Materials, vol. 7 (Jun. 2008) 442-453.
Aswal, V. K. et al., *Role of different counterions and size of micelle in concentration dependence micellar structure of ionic surfactants*, Chemical Physics Letters 368, (2003) 59-65.
Bigioni, T. P. et al., Kinetically driven self assembly of highly ordered nanoparticle monolayers, *Nature Materials*, vol. 5, (Apr. 2006) 265-270.
Bishop, K. J. M. et al., *Nanoscale Forces and Their Uses in Self-Assembly*, Small, vol. 5, No. 14 (2009) 1600-1630.
Cao, C. et al., *Metamaterials-Based Label-Free Nanosensor for Conformation and Affinity Biosensing*, ACS Nano (2013) 20 pages.
Cao, Q. et al., *Hydrogen-Bonding-Induced Colorimetric Detection of Melamine by Nonaggregation-Based Au-NPs as a Probe*, Biosensors and Bioelectronics vol. 25 (2010) 2680-2685.

(Continued)

*Primary Examiner* — Dah-Wei D. Yuan
*Assistant Examiner* — Jose Hernandez-Diaz
(74) *Attorney, Agent, or Firm* — Alston & Bird LLP

(57) ABSTRACT

Provided is a method of forming a monolayer of nanorods on a substrate, wherein the nanorods are at least substantially vertically aligned, the method including providing a droplet of a solution including the nanorods on a substrate, and controlling the temperature and the evaporation of the solution such that the internal region of the droplet is kept at near equilibrium status to allow formation of the monolayer of nanorods. Also provided is a monolayer of nanorods on the substrate thus obtained. Also provided is an optical arrangement and use of the optical arrangement.

15 Claims, 18 Drawing Sheets

(56) References Cited

OTHER PUBLICATIONS

Coenen, T. et al., *Directional Emission from Plasmonic Yagi-Uda Antennas Probed by Angle-Resolved Cathodoluminescence Spectroscopy*, Nano Letters, vol. 11 (2011) 3779-3784.
Dodson, S. et al., *Optimizing Electromagnetic Hotspots in Plasmonic Bowtie Nanoantennae*, Journal of Physical Chemistry Letter, vol. 4 (2013) 496-501.
Ehling, S. et al., *High-Performance Liquid Chromatographic Method for the Simultaneous Detection of the Adulteration of Cereal Flours with Melamine and Related Triazine by-Products Ammeline, Ammelide, and Cyanuric Acid*, Food Addititives and Contaminants, vol. 24, No. 12 (Dec. 2007) 1319-1325.
Funston, A. M. et al., *Plasmon Coupling of Gold Nanorods at Short Distances and in Different Geometries*, Nano Letters, vol. 9, No. 4 (2009) 1651-1658.
Guerrero-Martínez, A. et al., *Gemini-Surfactant-Directed Self-Assembly of Monodisperse Gold Nanorods into Standing Superlattices*, Angewandte Chemie, Int. Ed., vol. 48 (2009) 9484-9488.
Huang, G. et al., *High-Throughput Trace Melamine Analysis in Complex Mixtures*, Chem. Commun. (2009) 556-558.
International Search Report and Written Opinion for corresponding International Application No. PCT/SG2014/000107, dated May 29, 2014.
Jackson, J. B. et al., *Surface-Enhanced Raman Scattering on Tunable Plasmonic Nanoparticle Substrates*, Proc. Natl. Acad. Sci. vol. 101, No. 52 (Dec. 2004) 17930-17935.
Jurgens, B. et al., *Melem (2,5,8-Triamino-Tri-S-Triazine), an Important Intermediate During Condensation of Melamine Rings to Graphitic Carbon Nitride: Synthesis, Structure Determination by X-Ray Powder Diffractometry, Solid-State Nmr, and Theoretical Studies*, J. Am. Chem. Soc., vol. 125 (2003) 10288-10300.
Karpfen, A. et al., *On Blue Shifts of C—H Stretching Modes of Dimethyl Ether in Hydrogen- and Halogen-Bonded Complexes*, Elsevier, Chemical Physics Letters, vol. 431 (2006) 428-433.
Kennedy, S., *Epidemiology, Why Can't We Test Our Way to Absolute Food Safety?*, Science, vol. 322 (Dec. 2008) 1641-1643.
Larkin, P., *Infrared and Raman Spectroscopy: Principles and Spectral Interpretation*, Elsevier, (2011) 239 pages.
Li, J. F. et al., *Shell-Isolated Nanoparticle-Enhanced Raman Spectroscopy*, Nature, vol. 464 (Mar. 2010) 392-395.
Lim, D. K. et al., *Highly Uniform and Reproducible Surface-Enhanced Raman Scattering from DNA-Tailorable Nanoparticles with 1-Nm Interior Gap*, Nat. Nanotechnol, (May 2011) 25 pages.
Liu, X. R. et al., *Raman Spectroscopy of Melamine at High Pressures*, International Conference on High Pressure Science and Technology, Joint Airapt-22 and Hpcj-50, Journal of Physics Series 215 (2010) 6 pages.
Lyche, J. L. et al., *Reproductive and Developmental Toxicity of Phthalates*. Journal of Toxicology and Environmental Health, Part B: Critical Reviews (2009) 225-249.
Ming, T. et al., *Ordered Gold Nanostructure Assemblies Formed by Droplet Evaporation*, Angewandte Chemie, Int. Ed. (2008) 9831-9836.
Ming, T. et al., *Strong Polarization Dependence of Plasmon-Enhanced Fluorescence on Single Gold Nanorods*, Nano Letters, vol. 9, No. 11, (2009) 3896-3903.
Moon, G. D. et al., *Assembled Monolayers of Hydrophilic Particles on Water Surfaces*, ACS Nano (2011) 8600-8612.
Ng, K. C. et al., *Free-Standing Plasmonic-Nanorod Super Lattice Sheets*, ACS Nano (2012) 925-934.
Nie, S. et al., *Probing Single Molecules and Single Nanoparticles by Surface-Enhanced Raman Scattering*, Science, vol. 275 (Feb. 1997) 1102-1106.
Nikoobakht, B. et al., *Self-Assembly of Gold Nanorods*, Journal of Physical Chemistry B, vol. 104, No. 36 (2000) 8635-8640.
Norbygaard, T. et al., *Analysis of Phthalate Ester Content in Poly(Vinyl Chloride) Plastics by Means of Fourier Transform Raman Spectroscopy*, Applied Spectroscopy, vol. 58, No. 4, (2004) 410-413.
Novotny, F. et al., *Gold Nanorod Arrays: Optical Properties*, NanoCon 2012, (Oct. 23-25, 2012) 5 pages.
Ohshima, H. et al., *Electrostatic Interaction between TwoCylindrical Soft Particles*, Journal of Colloid and Interface Science, vol. 333 (2009) 202-208.
Panicker, C. Y. et al., *Ft-Ir, Ft-Raman and SersSpectra of Vitamin C*, Spectroc. Acta Pt. A—Molec. Biomolec. Spectr, vol. 65 (2006) 802-804.
Park, W. H. et al., *Charge Transfer Enhancement in the Sers of a Single Molecule*, Nano Letters vol. 10 (2010) 4040-4048.
Peng, B. et al., *Fluorophore-Doped Core-Multishell Spherical Plasmonic Nanocavities: Resonant Energytransfer toward a Loss Compensation*, ACS Nano Nanocavities: Resonant Energytransfer vol. 6, No. 7 (2012) 6250-6259.
Peng, B. et al., *Self-Healing Self-Assembly of Aspect-Ratio-Tunable Chloroplast-Shaped Architectures*, Crystal Growth & Design, vol. 9 (2009) 4745-4751.
Peng, B. et al., *Surfactant-Free Self-Assemblyof Nanocrystals into Ellipsoidal Architectures*, ChemPhysChem, vol. 11 (2010) 3744-3751.
Peng, B. et al., *Vertically Aligned Gold Nanorod Monolayer on Arbitrary Substrates: Self-Assembly and Femtomolar Detection of Food Contaminants*, ACS Nano, (Jun. 22, 2013) 8 pages.
Sau, T. K. et al., *Self-Assmbly Patterns Formed Upon Solvent Evaporation of Aqueous Cetyltrimethylammonium Bromide-Coated Gold Nanoparticles of Various Shapes*, Langmuir, vol. 21, No. 7 (2005) 2923-2929.
Tschirner, N. et al., *Resonance Roman Spectra of Beta-Carotene in Solution and in Photosystems Revisited: An Experimental and Theoretical Study*, Phys. Chem. Chem. Phys., vol. 11 (Aug. 2009) 11471-11478.
Wang, L. F. et al., *Ultra-Fast Spreading on Superhydrophilic Fibrous Mesh with Nanochannels*, Elsevier, Applied Surface Science, vol. 255 (2009) 4944-4949.
Xie, Y. et al., *Controllable Two-Stage Droplet Evaporation Method and Its Nanoparticle Self-Assembly Mechanism*, Langmuir, vol. 29 (2013) 6232-6241.
Xie, Y. et al., *Self-Assembly of Gold Nanorods into Symmetric Superlattices Directed by Oh-Terminated Hexa (Ethylene Glycol) Alkanethiol*, Langmuir, vol. 27 (2011) 11394-11400.
Xu, X. et al., *Flexible Visible-Infrared Metamaterials and Their Applications in Highly Sensitive Chemical and Biological Sensing*, Nano Letters, vol. 11 (2011) 3232-3238.
Yonzon, C. R. et al., *A Glucose Biosensor Based on Surface-Enhanced Raman Scattering: Improved Partition Layer, Temporal Stability, Reversibility, and Resistance to Serum Protein Interference*, Analytical Chemistry, vol. 76 (Jan. 2004) 78-85.
Young, K. L. et al., *Assembly of reconfigurable one-dimensional colloidal superlattices due to a synergy of fundamental nanoscale forces*, Proc. Natl. Acad. Sci., vol. 109, No. 7, (Feb. 14, 2012) 2240-2245.
Notification to Grant Patent Right for Chinese Application No. 201480017158.8 dated Aug. 2, 2017.
Office Action for Chinese Application No. 201480017158.8 dated Jul. 28, 2016.

* cited by examiner

R: Electrostatic repulsive force
A: van der Waals and depletion attractive force

MONOLAYER OF NANORODS ON A SUBSTRATE AND METHOD OF FORMING THE SAME

CROSS-REFERENCE TO RELATED APPLICATION

This application is a national phase entry of PCT/SG2014/000107, filed on 5 Mar. 2014, which claims the benefit of the US provisional patent application No. 61/773,617, filed on 6 Mar. 2013, the entire contents of both are incorporated herein by reference in their entirety for all purposes.

TECHNICAL FIELD

Various embodiments relate to a monolayer of nanorods on a substrate and a method of forming the same. Various embodiments further relate to an optical arrangement and use of the optical arrangement.

BACKGROUND

Food and drink safety is one of the most urgent needs in our daily life, and recently, food and drink safety has attracted great public attention, especially since the occurrence of *Escherchia coli* O157:H7 in beef, the occurrence of the dioxin egg scandal and recent scandals of melamine in infant formula and plasticizers in food and drinks.

Phthalate is known as an endocrine disrupter which produces reproductive and developmental toxicity, which may cause miscarriage, fewer motile sperm and external sex organs malformation of infant. Melamine, known as a triazine heterocyclic organic chemical material, can block and damage renal cells, resulting in kidney malfunction, and even death in infants. Such foodborne hazards come either from environmental hazards, e.g. contamination of phthalate plasticizers from processing equipment such as piping or container, or from illegal addition driven by economic benefit, e.g. melamine in infant formula and plasticizer contaminations in food and drinks in recent times. Public attention to food scandals raises an urgent need for detecting food contaminants and has imposed a pressing demand for rapid, inexpensive but effective and reliable methods to detect the food contaminations.

However, the current available techniques or prevailing detections are primarily based on liquid chromatography (e.g. high performance liquid chromatography (HPLC)), mass spectroscopy (MS) or colorimetric methods, which are restricted by sophisticated and time-consuming steps, inadequate detection limits and sample preparation which may include complicated sample pretreatment steps such as extraction, preconcentration, and derivatization.

Surface enhanced Raman scattering (SERS) spectroscopy may also be used for detection purposes. SERS spectroscopy is an extremely sensitive analytical technology used to detect and identify molecules, and is capable of providing highly resolved specific vibrational molecular information, and requires little sample preparation. The essential idea towards high sensitivity SERS detection is the engineering of noble metal containing substrates for achieving a highly localized electromagnetic field, which leads to a very strong electromagnetic enhancement. It has been shown that an enhancement factor (EF) value between $1 \times 10^6$ and $1 \times 10^8$ is adequate to achieve single molecule detection. In the past decades, many developments have been achieved on SERS-active nanostructures, such as gold (Au) and silver (Ag) nanoparticles, nanoshell, and colloidal metal nanoparticles arrays. However, many SERS-active substrates suffer from poor reproducibility of "hot spots", which refer to regions of enhanced electric field. It is thus a major challenge to reproducibly prepare stable SERS substrates with uniform "hot-spots" and controllably push the interior gap between nanostructures to sub-nm regime.

There is therefore need for a detection strategy that exhibits high sensitivity and specificity, requires a minimal sample preparation with rapid detection and low-cost.

SUMMARY

In a first aspect of the invention, a method of forming a monolayer of nanorods on a substrate is provided, wherein the nanorods are at least substantially vertically aligned. The method may include providing a droplet of a solution comprising said nanorods on a substrate, and controlling the temperature and the evaporation of the solution such that the internal region of the droplet is kept at near equilibrium status to allow formation of the monolayer of nanorods.

In a second aspect of the invention, a monolayer of nanorods on a substrate is provided. The monolayer of nanorods on the substrate may be obtained according to the method as described above.

In a third aspect of the invention, an optical arrangement is provided. The optical arrangement may include a substrate, and a monolayer of nanorods on the substrate, wherein the nanorods are at least substantially vertically aligned, and wherein an edge-to-edge spacing between adjacent nanorods is equal to or less than about 15 nm.

In a fourth aspect of the invention, use of the optical arrangement as described above for detection of at least one of an organic compound, a virus, a protein or a nucleic acid is provided.

In a fifth aspect of the invention, use of the optical arrangement as described above in a Raman spectroscopy device is provided.

BRIEF DESCRIPTION OF THE DRAWINGS

In the drawings, like reference characters generally refer to like parts throughout the different views. The drawings are not necessarily to scale, emphasis instead generally being placed upon illustrating the principles of the invention. In the following description, various embodiments of the invention are described with reference to the following drawings, in which:

FIG. 4C shows a scanning electron microscopy (SEM) image of an array of gold (Au) nanorods before UV ozone treatment, while

DETAILED DESCRIPTION

Figures 1A, 1B:
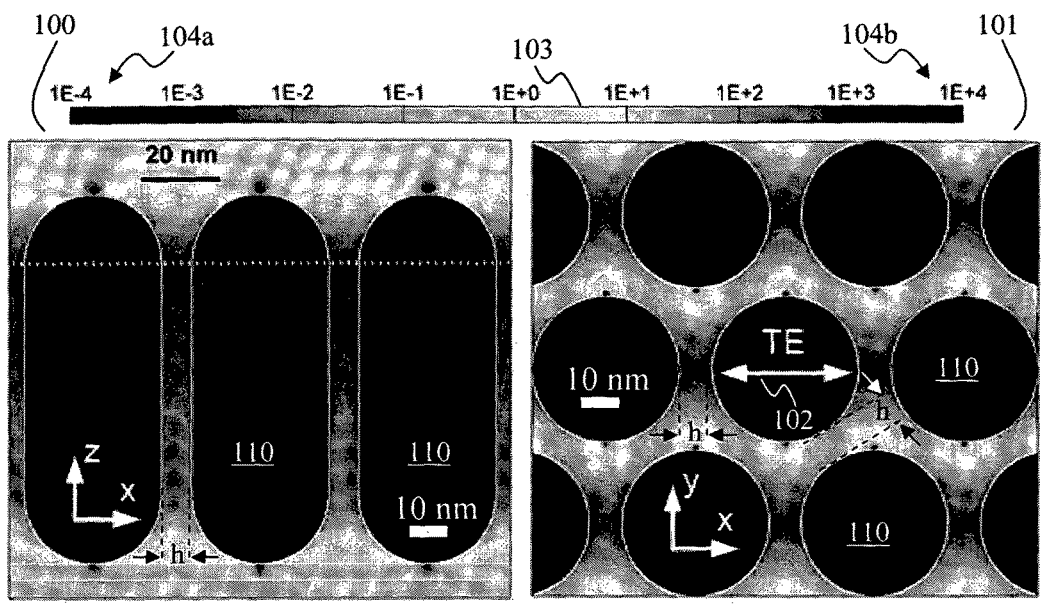
FIGS. 1A and 1B show local electric field simulation results for a hexagonal vertical gold (Au) nanorod array with an edge-to-edge spacing, h, of about 7.7 nm.

The following detailed description refers to the accompanying drawings that show, by way of illustration, specific details and embodiments in which the invention may be practiced. These embodiments are described in sufficient detail to enable those skilled in the art to practice the invention. Other embodiments may be utilized and structural, logical, and electrical changes may be made without departing from the scope of the invention. The various embodiments are not necessarily mutually exclusive, as some embodiments can be combined with one or more other embodiments to form new embodiments.

Embodiments described in the context of one of the methods or devices are analogously valid for the other methods or devices. Similarly, embodiments described in the context of a method are analogously valid for a device, and vice versa.

Features that are described in the context of an embodiment may correspondingly be applicable to the same or similar features in the other embodiments. Features that are described in the context of an embodiment may correspondingly be applicable to the other embodiments, even if not explicitly described in these other embodiments. Furthermore, additions and/or combinations and/or alternatives as described for a feature in the context of an embodiment may correspondingly be applicable to the same or similar feature in the other embodiments.

In the context of various embodiments, the articles "a", "an" and "the" as used with regard to a feature or element include a reference to one or more of the features or elements.

In the context of various embodiments, the phrase "at least substantially" may include "exactly" and a reasonable variance.

In the context of various embodiments, the term "about" or "approximately" as applied to a numeric value encompasses the exact value and a reasonable variance.

As used herein, the term "and/or" includes any and all combinations of one or more of the associated listed items.

As used herein, the phrase of the form of "at least one of A or B" may include A or B or both A and B. Correspondingly, the phrase of the form of "at least one of A or B or C", or including further listed items, may include any and all combinations of one or more of the associated listed items.

Various embodiments may provide a vertically-aligned monolayer of gold (Au) nanorods on arbitrary substrates. The vertically-aligned monolayer of Au nanorods formed using methods of various embodiments on a substrate may be used, for example, for femtomolar detection of organic compounds such as phthalate plasticizers.

Various embodiments may provide a method of forming or assembling nanorods (e.g. gold (Au) nanorods) on a substrate, and an optical arrangement formed by the method. The nanorods may be at least substantially vertically aligned relative to a surface of the substrate from which the nanorods extend. The method may include a self-assembly process of the nanorods on the substrate. The self-assembly may occur in an internal region of a droplet containing the nanorods provided onto the substrate, where a near-equilibrium status may be formed within the internal region of the droplet. The van der Waals and depletion attractive forces may push the nanorods to approach each other, while the electrostatic repulsive forces may urge the nanorods to move away from each other. Therefore, the synergy between the repulsive force and the attractive force may ensure alignment of the nanorods at the equilibrium status, rather than random aggregation of the nanorods. The equilibrium status may be maintained by controlling the evaporation of the solution contained in the droplet. The temperature of the solution may be controlled to control the evaporation of the solution. Further, the humidity of the environment the solution is exposed to may be controlled to control the evaporation of the solution. In a non-limiting example, this may be done by keeping respective samples of the substrates with the droplets in an enclosure (e.g. a Petri dish) with a cover at a temperature of about 21° C. and a humidity of >60%. These factors, including the cover, the temperature and the humidity may be taken into consideration so as to allow formation of a monolayer array of vertically aligned nanorods on the substrate. The evaporation rate of the solvent of the droplet and the Brownian motion of the nanorods should be sufficiently slow, so as to ensure that the near-equilibrium status at the internal region of the droplet may be kept for a long time and there is enough time for the nanorods to self-assemble in a side-by-side model.

In various embodiments, a monolayer of vertically aligned gold (Au) nanorods may be formed on the substrate. The Au nanorods may be coated with a surfactant, for example hexadecyltrimethylammonium bromide (CTAB). For CTAB-coated Au nanorods, the electrostatic interactions may be decreased by removing the CTAB molecules on the surface of the Au nanorods, where a shrinkage of the edge-to-edge spacing or edge-to-edge separation between adjacent Au nanorods to a sub-nm regime, for example approximately 0.8 nm, may be achieved. The sub-nm edge-to-edge gap distance has a non-trivial consequence, as the local electromagnetic field enhancement may be enhanced considerably, leading to exceptionally strong surface enhanced Raman scattering (SERS) signals, for example, of plasticizers down to femtomolar (fM) in commercial orange juice samples.

Various embodiments may provide a facile strategy to assemble a vertically-aligned monolayer of Au nanorods, in which the assembled Au nanorods may be used for applications in rapid detection of plasticizers and melamine contamination at, for example, a femtomolar level by surface-enhanced Raman scattering (SERS) spectroscopy. The SERS signals of plasticizers may be sensitive down to approximately 0.9 fM concentrations in samples of orange juices. This may be the lowest detection limit to date, which is about 7 orders of magnitude lower than the standard applicable to the United States (which is ~6 ppb). The highly organized vertical arrays of Au nanorods may generate reproducible "SERS-active sites", and may be achieved on arbitrary substrates, including but not limited to silicon (Si), gallium nitride (GaN), glass and flexible poly(ethylene naphthalate) (PEN) substrates.

A vertical monolayer geometry of Au nanorods may exhibit highly uniform hot spots, which are regions of enhanced electric field. The anisotropic shape of Au nanorods may provide the array of vertical Au nanorods with a strong nanoantenna effect. Finite-difference time-domain method (FDTD) simulation shows that a monolayer of hexagonally-packed Au nanorod array may exhibit strong and uniform local electromagnetic fields.

FIGS. 1A and 1B show local electric field simulation results for a vertical gold (Au) nanorod array in a hexagonally packed configuration with an edge-to-edge spacing (or gap distance), h, of about 7.7 nm, illustrating results for local electric field enhancement factor. FIG. 1A shows a local electromagnetic field enhancement contour plot 100 for a cross-sectional region of the array of Au nanorods 110 along a vertical plane (x-z plane) while FIG. 1B shows a local electromagnetic field enhancement contour plot 101 for a cross-sectional region of the array of Au nanorods 110 along a horizontal plane (x-y plane) (or a top-view plane along the y-axis), when an incident plane wave in transverse electric (TE) polarization is provided. The arrow indicated with "TE" and represented by 102 shows the polarization of a 785 nm laser incident on the Au nanorods 110.

Figures 1C, 1D:
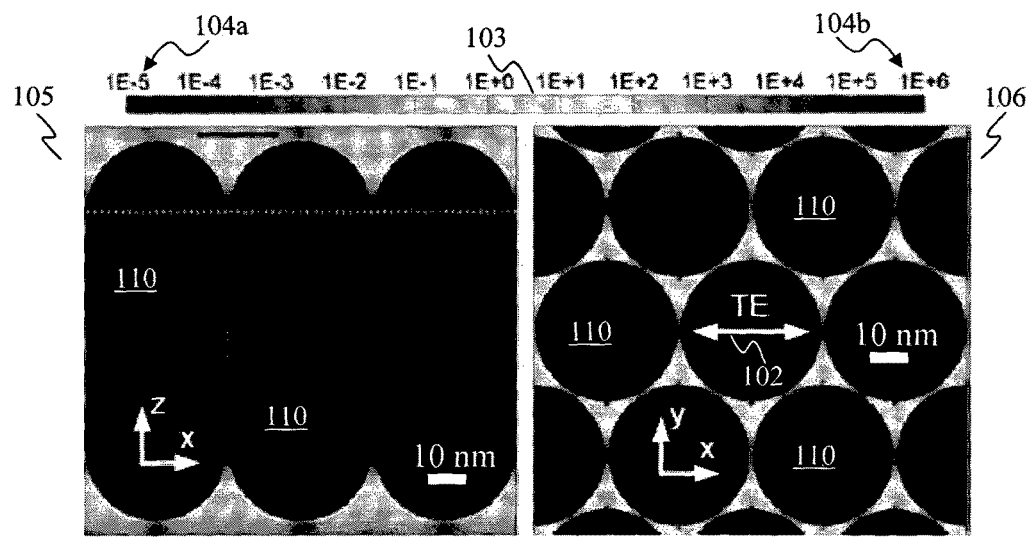
FIGS. 1C and 1D show local electric field simulation results for a hexagonal vertical gold (Au) nanorod array with an edge-to-edge spacing, h, of about 0.8 nm.

FIGS. 1C and 1D show local electric field simulation results for a vertical gold (Au) nanorod array in a hexagonally packed configuration with an edge-to-edge spacing (or separation), h, of about 0.8 nm, illustrating results for local electric field enhancement factor. FIG. 1C shows a local electromagnetic field enhancement contour plot 105 for a cross-sectional region of the array of Au nanorods 110 along a vertical plane (x-z plane) while FIG. 1D shows a local electromagnetic field enhancement contour plot 106 for a cross-sectional region of the array of Au nanorods 110 along a horizontal plane (x-y plane) (or a top-view plane along the y-axis), when an incident plane wave in transverse electric (TE) polarization is provided. The arrow indicated with "TE" and represented by 102 shows the polarization of a 785 nm laser incident on the Au nanorods 110.

For all the contour plots 100, 101, 105, 106, the value of the electric field enhancement factor associated with the Au nanorods 110 is towards the lower end 104a of the scale 103 while the electric field enhancement factor in the edge-to-edge spacing regions or gaps (with distance, h) between the Au nanorods 110 has a value towards the upper end 104b of the scale 103.

Figure 1E:
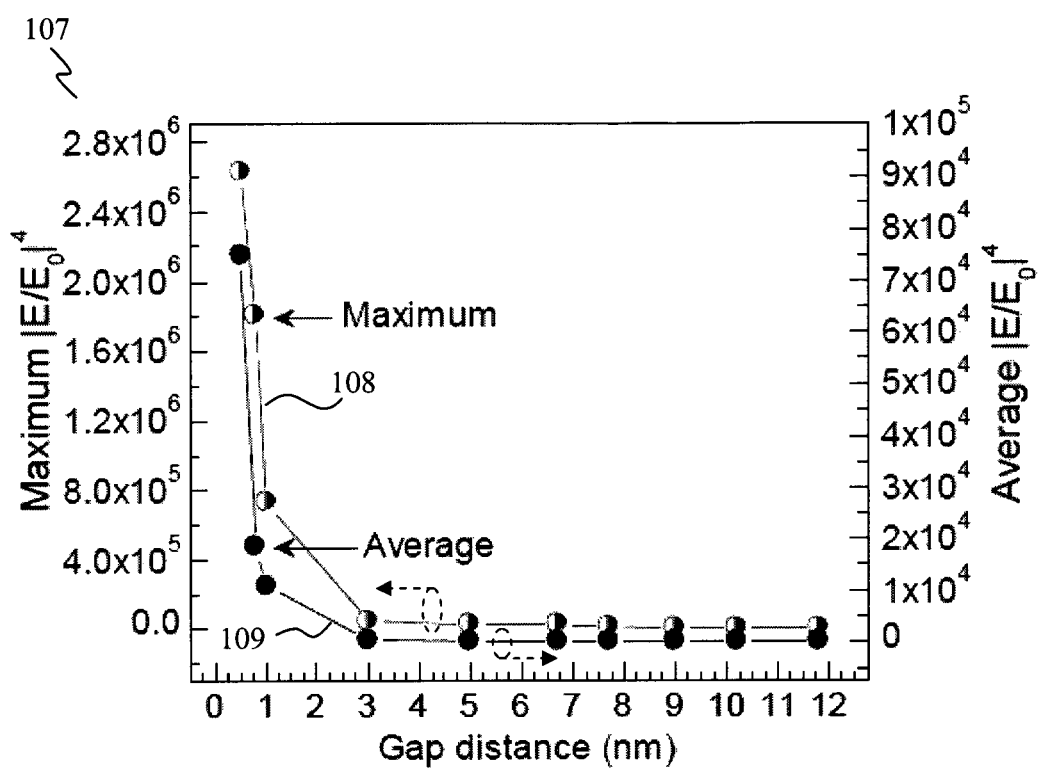
FIG. 1E shows a plot of the volume maximum and the volume average electric field enhancement factors, $|E/E_0|^4$, as a function of the edge-to-edge spacing, h, between two adjacent Au nanorods.

The local electric field enhancement factor may be defined as $|E/E_0|^4$, where $|E|$ and $|E_0|$ are magnitudes of the local electric field, and the incident electric field, respectively. The electric fields may be spatially confined into the gap between adjacent Au nanorods 110 to provide a homogeneous and strong near-field localization in three-dimensional (3D) spatial structures. FIG. 1E shows a plot 107 of the volume maximum (represented as 108) and the volume average (represented as 109) electric field enhancement factors, $|E/E_0|^4$, as a function of the edge-to-edge spacing (or gap distance), h, between two adjacent Au nanorods 110. As may be observed, the maximum $|E/E_0|^4$ is around $2.6 \times 10^6$, $1.8 \times 10^6$ and $7.4 \times 10^5$ when the gap size, h, is about 0.5, 0.8 nm and 1.0 nm, respectively.

Further, both the maximum and the average $|E/E_0|^4$ decrease with an increase in the separation distance, h, which may indicate that a decrease in the gap size, h, may improve the enhancement factor (EF) and the sensitivity of SERS. In addition, the gaps between the nanorod "forest" or array may trap liquid samples due to capillary force, which is another advantage of the vertical Au nanorod arrays for SERS. Therefore, highly organized arrays of vertical Au nanorods or a vertical monolayer of Au nanorods may act as extended nanoantennae to generate a strong, reproducible and highly homogeneous distribution of electric fields, which may provide facile and reproducible SERS substrates that may be an improvement over prior art nanoparticle substrates.

Figure 2A:
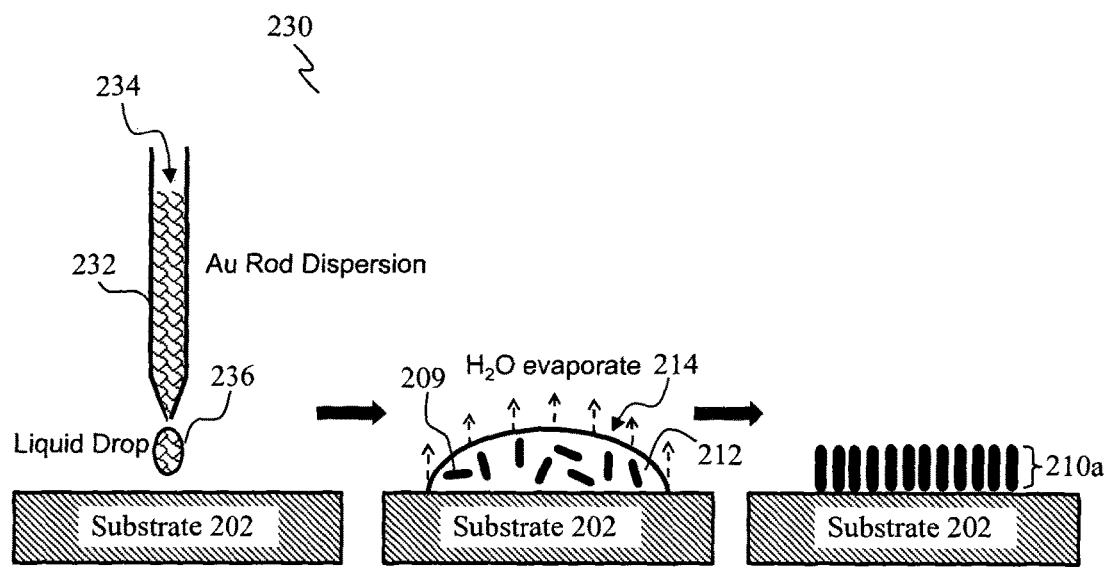
FIG. 2A shows various processing stages of a method of forming a monolayer of nanorods on a substrate, according to various embodiments.
Figure 2B:
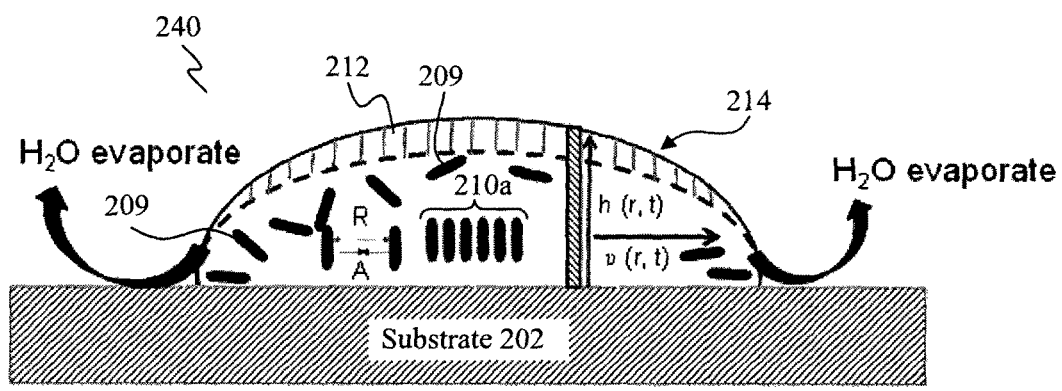
FIG. 2B shows a schematic diagram of a self-assembly process of nanorods on a substrate, according to various embodiments.

FIG. 2A shows various processing stages of a method 230 of forming a monolayer of nanorods on a substrate (e.g. silicon substrate) 202, according to various embodiments. FIG. 2B shows a schematic diagram 240 of a self-assembly process of nanorods 209 on a substrate (e.g. silicon substrate) 202, according to various embodiments, for illustrating an equilibrium or near equilibrium status of nanorods 209 in an internal region of a droplet 214. Using gold (Au) nanorods as a non-limiting example, a dispenser (e.g. a pipette) 232 containing a gold (Au) nanorod dispersion 234 may be provided. As an example, the Au nanorod dispersion 234 may include Au nanorods dispersed in an aqueous solution (e.g. sodium chloride (NaCl) aqueous solution). The dispenser 232 may dispense a liquid drop 236 of the Au nanorod dispersion 234 onto a substrate 202 to form a droplet 214 on the substrate 202. Therefore, the droplet 214 contains a dispersion of gold (Au) nanorods 209, in an aqueous solution (e.g. sodium chloride (NaCl) aqueous solution) 212. Water in the aqueous solution 212 may evaporate, causing a decrease in the size of the droplet 214, for example as shown in FIG. 2B, from the size outlined by the solid line to the size outlined by the dashed line. At the same time, free Au nanorods 209 may assemble to form monolayer arrays 210a, which may then precipitate to stand up on the substrate 202 due to gravity and van der Waal's interactions to the host substrate 202. During the self-assembly process, in the internal region of a droplet 214, the van der Waals and depletion attractive forces (A) may push the nanorods 209 to approach each other, while the electrostatic repulsive forces (R) may urge the nanorods 209 to move away from each other. The synergy between the repulsive force (R) and the attractive force (A) may ensure alignment of the nanorods 209 to allow formation of a monolayer of nanorods 210a at the equilibrium status. The water evaporation rate may be controlled so as to ensure that the internal region of the droplet 214 may be kept at near equilibrium status to allow formation of a monolayer of nanorods 210a on the substrate 202. In FIG. 2B, the notation "h(r,t)" refers to the height of the droplet 214 at location "r" and time "t", where "r" is the distance from the droplet center to location "r", while the notation "v(r,t)" refers to the liquid moving velocity from location "r" to the droplet edge.

Figure 2C:
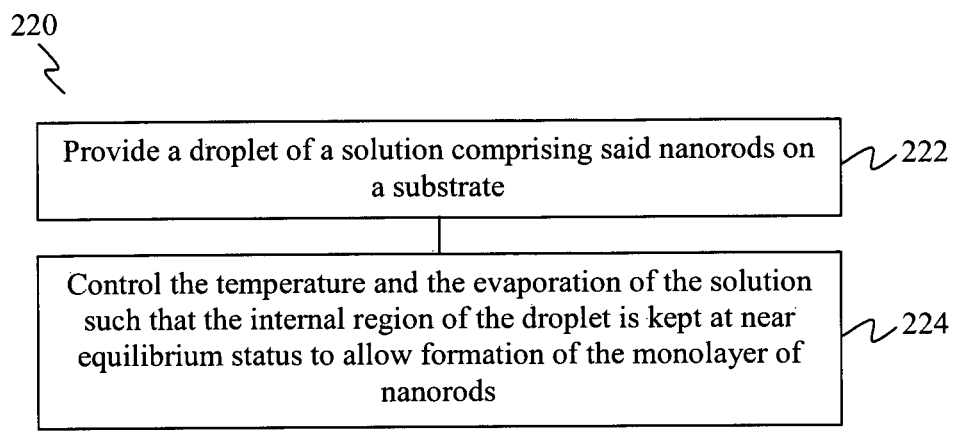
FIG. 2C shows a flow chart illustrating a method of forming a monolayer of nanorods on a substrate, wherein the nanorods are at least substantially vertically aligned, according to various embodiments.

FIG. 2C shows a flow chart 220 illustrating a method of forming a monolayer (or a single layer) of nanorods on a substrate, wherein the nanorods are at least substantially vertically aligned, according to various embodiments.

At 222, a droplet of a solution including said nanorods is provided on a substrate. In various embodiments, the solution may be an aqueous solution. The solvent in the solution may be water.

At 224, the temperature and the evaporation of the solution are controlled such that the internal region of the droplet is kept at near equilibrium status to allow formation of the monolayer of nanorods.

In the context of various embodiments, the nanorods being at least substantially vertically aligned may mean that the nanorods may be arranged at least substantially perpendicular relative to the substrate surface and arranged parallel to each other. In other words, this may mean that the nanorods may be formed on the substrate at least substantially perpendicular to the surface of the substrate from which the nanorods extend.

In various embodiments, controlling the temperature and the evaporation of the solution may allow the evaporation rate of the solvent of the solution and the Brownian motion of the nanorods to be sufficiently slow, so as to maintain a near equilibrium status at the internal region of the droplet for a sufficiently long time, such that there may be enough time for the nanorods to self-assemble in a side-by-side arrangement on the substrate. In this way, the method may provide an evaporation-induced self-assembly approach to form a monolayer of vertically aligned nanorods on the substrate.

In various embodiments, at 224, the solution may be exposed to a temperature of between about 5° C. and about 25° C., for example between about 5° C. and about 21° C., between about 5° C. and about 15° C., between about 10° C. and about 25° C., between about 15° C. and about 25° C., or between about 20° C. and about 25° C. For example, the solution may be exposed to a temperature of about 21° C.

In various embodiments, the method may further include controlling the humidity of the environment the solution is exposed to. This may mean that the humidity of the environment may be controlled to control the evaporation of the solution. In various embodiments, the solution may be exposed to a humidity of about 60% or more (i.e. ≥60%), for example ≥70%, or between about 60% and about 80%, between about 60% and about 70%, e.g. about 61%.

In various embodiments, the temperature and the evaporation of the solution may be controlled by placing the substrate with the droplet in an enclosure. For example, the interior of the enclosure may be subjected to a temperature of between about 5° C. and about 25° C., e.g. 21° C. Further, the humidity of the environment in the enclosure may also be controlled. For example, the interior of the enclosure may be subjected to a humidity of about 60% or more. The substrate with the droplet may be placed in the enclosure for a duration of about 12 hours or more (i.e. ≥12 hours), for example ≥14 hours, ≥16 hours, or ≥18 hours, e.g. for about 12 hours. In the context of various embodiments, the enclosure may be a petri dish having a cover or lid to form an enclosed space within which the substrate may be placed.

The method may further include forming the nanorods, preparing an electrolyte solution, and mixing the nanorods and the electrolyte solution to form the solution that is provided on the substrate. In various embodiments, the electrolyte solution may include a monovalent compound, for example sodium chloride (NaCl), potassium chloride (KCl), potassium bromide (KBr), or sodium bromide (NaBr). The electrolyte solution may have a concentration that may be equal to or less than about 0.03 M (i.e. ≤0.03 M), e.g. ≤0.02 M, ≤0.01 M, or about 0.01 M.

In various embodiments, the nanorods may be formed by preparing a seed solution including a precursor material for the nanorods, preparing a growth solution including the precursor material, and mixing the seed solution and the growth solution.

In various embodiments, each nanorod may be free of a surfactant.

In various embodiments, each nanorod may include a surfactant coated on a surface of the nanorod. The surfactant may include hexadecyltrimethylammonium bromide (CTAB), or hexadecyltrimethylammonium chloride (CTAC). In various embodiments, the method may further include removing the surfactant, for example by carrying out an ultraviolet (UV) ozone treatment on the surfactant-coated nanorods. As a result of the UV ozone treatment, the surfactant may be at least substantially completely removed.

In various embodiments, the nanorods may be formed spaced apart from each other. An edge-to-edge spacing (or separation or gap distance), h, between adjacent nanorods may be equal to or less than about 15 nm (i.e. ≤15 nm). In the context of various embodiments, the terms "edge-to-edge spacing", "edge-to-edge separation" and "edge-to-edge gap distance" are defined as the spacing or gap distance, h, at the shortest or closest separation between adjacent nanorods.

While the method described above is illustrated and described as a series of steps or events, it will be appreciated that any ordering of such steps or events are not to be interpreted in a limiting sense. For example, some steps may occur in different orders and/or concurrently with other steps or events apart from those illustrated and/or described herein. In addition, not all illustrated steps, may be required to implement one or more aspects or embodiments described herein. Also, one or more of the steps depicted herein may be carried out in one or more separate acts and/or phases.

Various embodiments may also provide a monolayer of nanorods on a substrate obtained according to the method of various embodiments.

Figure 2D:
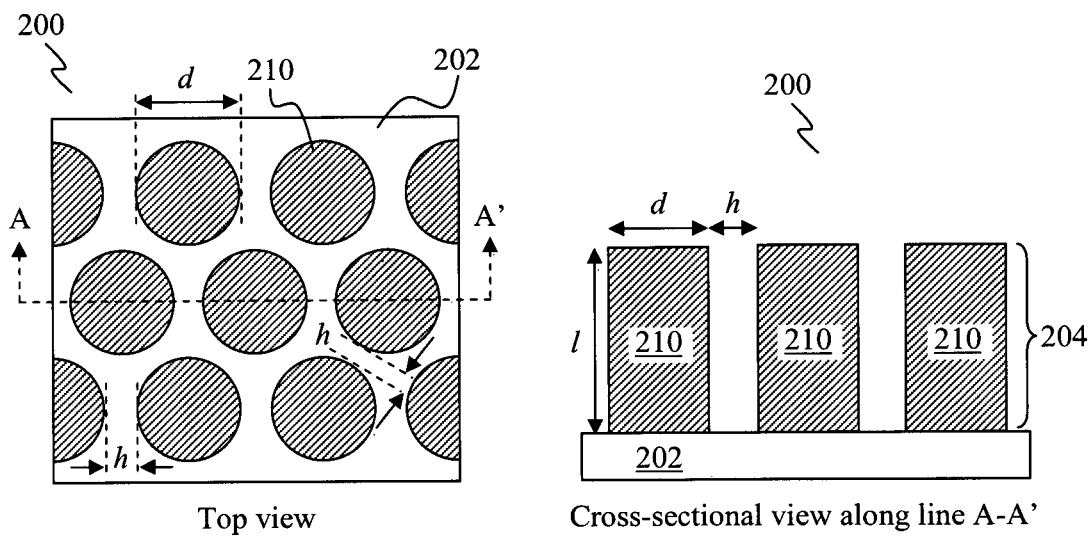
FIG. 2D shows a schematic top view and a schematic cross-sectional view of an optical arrangement, according to various embodiments.

FIG. 2D shows a schematic top view and a schematic cross-sectional view of an optical arrangement 200, according to various embodiments. The optical arrangement 200 includes a substrate 202, and a monolayer 204 of nanorods 210 on the substrate 202, wherein the nanorods 210 are at least substantially vertically aligned, and wherein an edge-to-edge spacing (or gap distance), h, between adjacent nanorods 210 is equal to or less than about 15 nm (i.e. ≤15 nm). The optical arrangement 200 may be formed using methods of various embodiments.

In various embodiments, the edge-to-edge spacing, h, may be equal to or less than about 12 nm (i.e. ≤12 nm), for example ≤10 nm or ≤8 nm.

In various embodiments, the edge-to-edge spacing, h, may be equal to or less than about 2 nm (i.e. ≤2 nm), for example about 1.7 nm.

In various embodiments, the edge-to-edge spacing, h, may be equal to or less than about 1 nm (i.e. ≤1 nm), for example between 0.6 nm and 1.0 nm, e.g. about 0.8 nm.

In various embodiments, the edge-to-edge spacing, h, may be between about 6 nm and about 12 nm, for example between about 6.7 nm and about 11.8 nm, e.g. about 6.7 nm, about 7.7 nm, about 7.9 nm, about 10.2 nm, or about 11.8 nm.

In the context of various embodiments, each nanorod 210 may be free of a surfactant.

In the context of various embodiments, each nanorod 210 may include a surfactant coated on a surface of the nanorod 210. The surfactant may be coated on the entire exposed surface of each nanorod 210. The surfactant may act as a capping material. The surfactant may be a stabilizing agent. The surfactant may induce growth of the nanorods 210 in a preferential direction or orientation during growth of the nanorods 210. In various embodiments, the surfactant may include hexadecyltrimethylammonium bromide (CTAB).

In the context of various embodiments, each nanorod 210 may have a diameter, d, or a cross-sectional width of between about 27 nm and about 46 nm, for example between about 27 nm and about 40 nm, between about 27 nm and about 35 nm, between about 30 nm and about 46 nm, between about 35 nm and about 46 nm, or between about 27.3 nm and about 45.4 nm.

In the context of various embodiments, each nanorod 210 may have a length, l, of between about 88 nm and about 101 nm, for example between about 88 nm and about 95 nm, between about 95 nm and about 101 nm, between about 90 nm and about 100 nm, between about 88.2 nm and about 100.5 nm.

In the context of various embodiments, the nanorods 210 may be arranged in a hexagonally packed configuration.

In the context of various embodiments, each nanorod 210 may be or may act as a plasmonic nanorod, where each nanorod may be capable of supporting a plasmon (e.g. a surface plasmon). This may mean that each nanorod may include or be made of a material that may be capable of supporting a plasmon (e.g. a surface plasmon).

In the context of various embodiments, each nanorod 210 may include at least one of gold (Au) or silver (Ag).

In the context of various embodiments, the substrate 202 may include at least one of a semiconductor, a glass or a polymer. The semiconductor substrate may include silicon (Si) or gallium nitride (GaN) (e.g. a GaN light emitting diode (LED) device). The glass substrate may include an indium tin oxide (ITO)-coated glass. The polymer substrate may include poly(ethylene naphthalate) (PEN). The polymer substrate may be flexible.

Various embodiments may also provide use of the optical arrangement 200 for detection of at least one of an organic compound, a virus, a protein or a nucleic acid (e.g. DNA).

In various embodiments, the organic compound to be detected may include at least one of a phthalate or melamine. Examples of phthalates include but not limited to Benzyl-butylphthalate (BBP, $C_{19}H_{20}O_4$), Bis(2-ethylhexyl)phthalate (DEHP, $C_{24}H_{38}O_4$), Dibutyl phthalate (DBP, $C_{16}H_{22}O_4$), and Diethyl Phthalate (DEP, $C_{12}H_{14}O_4$).

In various embodiments, the organic compound to be detected may have a concentration equal to or less than about 1 femtomolar (i.e. ≤1 fM), e.g. about 1 fM or about 0.9 fM.

In various embodiments, detection may be carried out by means of Raman spectroscopy, e.g. surface-enhanced Raman scattering spectroscopy.

Various embodiments may also provide use of the optical arrangement 200 in a Raman spectroscopy (e.g. surface-enhanced Raman scattering spectroscopy) device or system.

The process of various embodiments for self-assembly of gold (Au) nanorods into a vertically aligned monolayer will now be described by way of the following non-limiting examples.

An evaporation-induced self-assembly strategy may be employed to generate a vertically aligned monolayer of CTAB (hexadecyltrimethylammonium bromide)-stabilized Au nanorods based on a near-equilibrium status at an internal region of drying droplets, which may eliminate or at least minimise any complex ligand exchange reaction which may occur. The process may include synthesis of CTAB-coated Au nanorods, followed by evaporation-induced self-assembly of the CTAB-coated Au nanorods to form a vertically aligned monolayer on a substrate.

The synthesis of the CTAB-coated Au nanorods will now be described. Au nanorods were prepared using a seeded growth method with hexadecyltrimethylammonium bromide (CTAB) as a stabilizing agent. The seed solution was prepared by mixing an aqueous solution of fresh ice-cold $NaBH_4$ (Sodium borohydride) (0.6 ml, 0.01 M), $HAuCl_4$ (Chloroauric acid) (0.25 mL, 0.01 M) and CTAB (9.75 ml, 0.1 M). After rapid inversion for about 2 minutes, the seed solution was allowed to stand for about 2 hours at approximately 28° C. A growth solution was made by respectively adding aqueous solutions of $AgNO_3$ (Silver nitrate) (0.01 M, 0.4 mL), $HAuCl_4$ (Chloroauric acid) (0.01 M, 2 mL), ascorbic acid (0.1 M, 0.32 mL) and HCl (Hydrochloric acid) (1.0 M, 0.8 mL) into a CTAB aqueous solution (0.1 M, 40 mL). The seed solution (approximately 10 μL) was added into the growth solution to form a mixture solution. After a gentle inversion for about 10 seconds, the mixture solution was left undisturbed for about 16 hours. As a result, Au nanorods were formed and the Au nanorods were obtained by centrifugation, and re-dispersed in a CTAB aqueous solution (0.1 M, 40 mL).

The evaporation-induced self-assembly of the CTAB-coated Au nanorods to form a vertically aligned monolayer will now be described. Approximately 3 ml prepared Au nanorods were centrifugated at a speed of about 6000 rpm for about 10 minutes, and the precipitates were re-dispersed in a CTAB solution (2 ml, 2.5 mM) containing NaCl (Sodium chloride) whose concentration were approximately 0, 0.001, 0.004, 0.01, and 0.03 M, respectively. Then, approximately 10 μL dispersion of the CTAB-coated Au nanorods were dropped on arbitrary substrates, such as silicon (Si), glass, ITO (indium tin oxide) glass, GaN (gallium nitride) LED (light emitting diode) device, or flexible PEN (poly(ethylene naphthalate)) polymer, which were cleaned by acetone and isopropyl alcohol. The samples of the substrates with the CTAB-coated Au nanorods were kept in a petri dish with a cover at about 21° C. for about 12 hours. The humidity was approximately 61%, although a humidity of between about 60% and about 100% may be provided. As a result, a monolayer of vertically aligned Au nanorods was formed on the respective substrates.

For the purpose of SERS characterization, Raman scattering spectroscopy was conducted on the Au nanorod arrays of various embodiments using a micro-Raman spectrometer (Horiba-JY T64,000) excited with a solid state laser (wavelength, λ=785 nm) in a backscattering configuration. The backscattered signal was collected through a 100× objective and dispersed by a 1800 g/mm grating. The laser power on the sample surface was measured to be about 1.2 mW.

Examples of the array of Au nanorods that are formed aligned at least substantially perpendicularly or vertically on a substrate and the corresponding results will now be described.

Figure 3A:
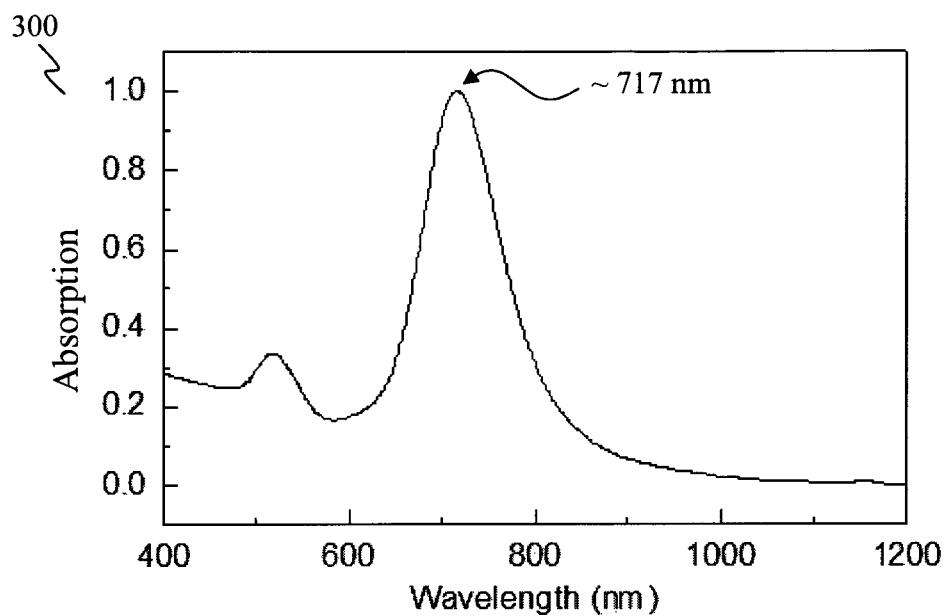
FIG. 3A shows a plot of an absorption spectrum of a gold (Au) nanorod aqueous solution.
Figure 3B:
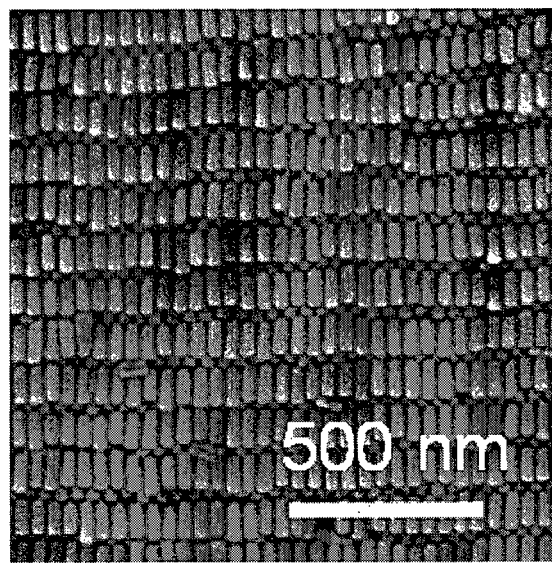
FIG. 3B shows a scanning electron microscopy (SEM) image of gold (Au) nanorods.
Figure 3C:
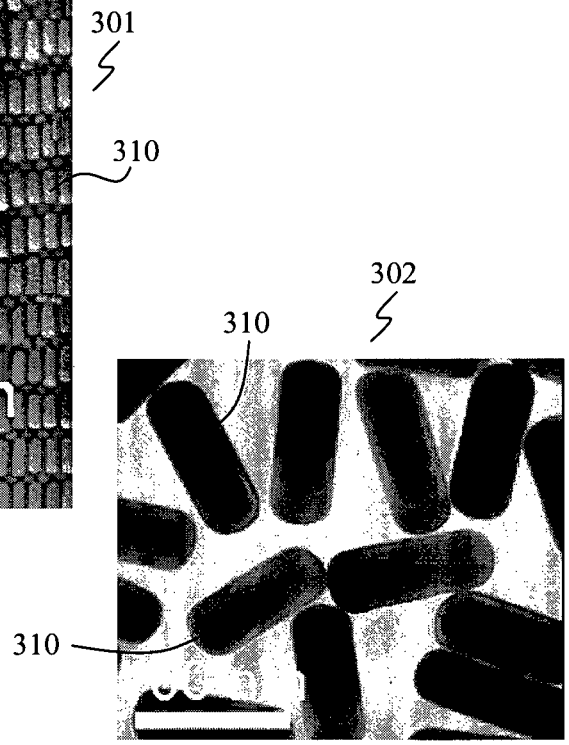
FIG. 3C shows a transmission electron microscopy (SEM) image of gold (Au) nanorods.

Gold (Au) nanorods having a length, l, of approximately 92.5 nm and a diameter, d, of approximately 34.3 nm were synthesized using CTAB as a stabilizer. CTAB may act as a surfactant that coats the surface of the Au nanorods. FIG. 3A shows a plot 300 of an absorption spectrum of a gold (Au) nanorod aqueous solution (e.g. Au nanorods dispersed in H$_2$O). Plot 300 shows that the longitudinal plasmon band of the Au nanorods is located at approximately 717 nm. FIGS. 3B and 3C show, respectively, a scanning electron microscopy (SEM) image 301 and a transmission electron microscopy (SEM) image 302 of the Au nanorods, as represented by 310. The scale bar in FIG. 3C represents 100 nm. The TEM image 302 shows that the Au nanorods 310 exhibit good size uniformity.

Approximately 10 μL of a Au nanorod aqueous dispersion containing NaCl (0.01 M) was dropped on Si substrates and kept in a petri dish at room temperature (approximately 21° C.). The water solvent of the aqueous dispersion was then allowed to evaporate through the gap or spacing between the base dish and the cover of the petri dish. After about 12 hours, vivid hexagonal vertical arrays of Au nanorods were formed, and the edge-to-edge spacing (or edge-to-edge gap distance), h, between adjacent Au nanorods was found to be approximately 7.7±0.4 nm.

Figure 4A:
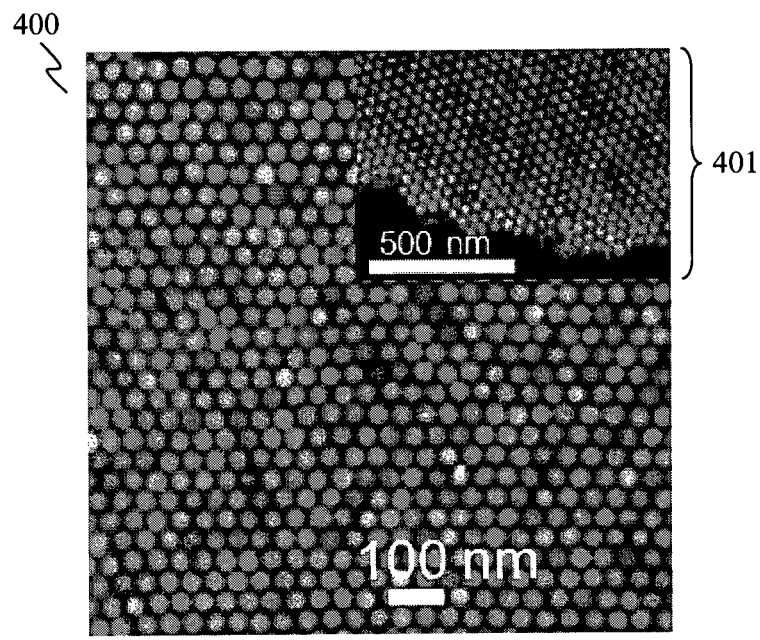
FIG. 4A shows a scanning electron microscopy (SEM) image illustrating a top view of an array of gold (Au) nanorods with an edge-to-edge spacing of about 7.7±0.4 nm.

FIGS. 4A to 4E show scanning electron microscopy (SEM) images of the formed-monolayer vertical Au nanorod array arranged in a hexagonal lattice (hexagonally packed configuration) and results illustrating the tuning of the separation or gap distance between adjacent Au nanorods. FIG. 4A shows a scanning electron microscopy (SEM) image 400 illustrating a top view of the Au nanorods with an edge-to-edge gap distance, h, of about 7.7±0.4 nm. The inset of FIG. 4A shows an SEM image 401 illustrating an edge view of the Au nanorod array. As may be observed from the SEM image 401, the array of Au nanorods is arranged in a monolayer fashion or in other words, as a monolayer feature.

In order to tune the spacing or separation, h, between adjacent Au nanorods that are assembled in a hexagonal vertical monolayer array, the ionic strength of a sample solution containing the Au nanorods may be adjusted to change the Debye length associated with the Au nanorodes dispersed in the solution. The ionic strength may be changed by means of addition of an electrolyte, for example. In a colloidal aqueous dispersion, the Debye length, $\kappa^{-1}$, for a symmetric monovalent electrolyte may be denoted by Equation 1:

$$\kappa^{-1}(nm)=0.3/\sqrt{I(M)} \quad \text{(Equation 1),}$$

where I is the ionic strength expressed in molar (M or mol/L). In various embodiments, sodium chloride (NaCl) may be used as the electrolyte to adjust the ionic strength.

The edge-to-edge separation, h, between Au nanorods may decrease as the Debye length decreases. When the Debye length is adjusted to be approximately 1.7 nm, the separation (or gap distance), h, between adjacent vertical Au nanorods may decrease to approximately 6.7±0.9 nm, which is approximately twice the length of a bilayer of the cationic surfactant CTAB. While not wishing to be bound, this value may be a lower limit that may be achieved in the assembly of the CTAB-coated Au nanorods.

Figure 4B:
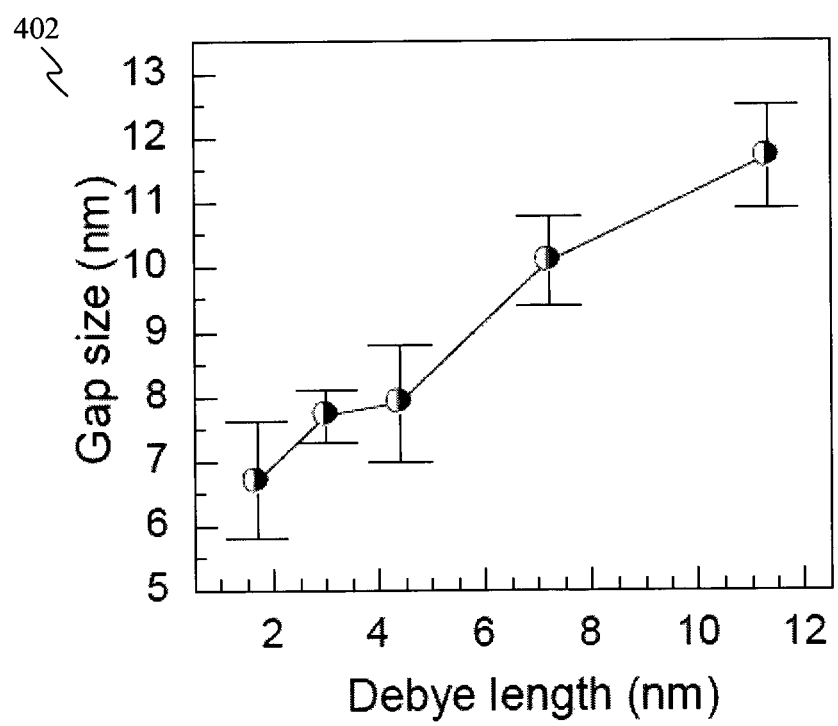
FIG. 4B shows a plot of measured edge-to-edge separation as a function of the Debye length.

FIG. 4B shows a plot of measured edge-to-edge separation, h, as a function of the Debye length, which is adjusted by changing the ionic strength. As may be observed, the spacing (gap size), h, between adjacent nanorods may be tuned to approximately 7.7±014 nm, 7.9±0.9 nm, 10.2±0.7 nm, and 11.8±0.8 nm when the Debye lengths for Au nanorod solutions are about 3.0 nm, 4.4 nm, 7.2 nm, and 11.3 nm, respectively.

Figure 4C:
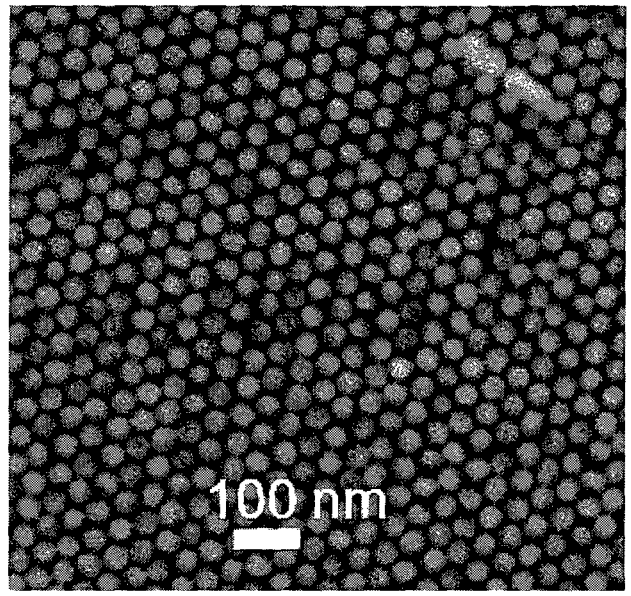
Figure 4D:
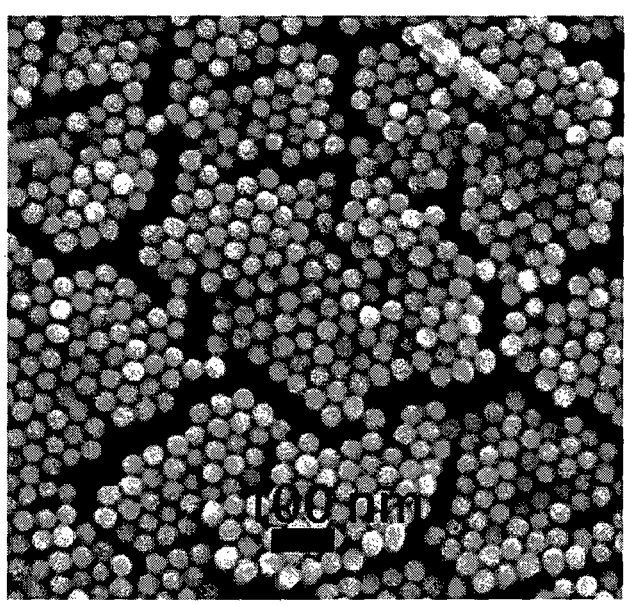
FIG. 4D shows a scanning electron microscopy (SEM) image of the array of gold (Au) nanorods of FIG. 4C after UV ozone treatment.
Figure 4E:
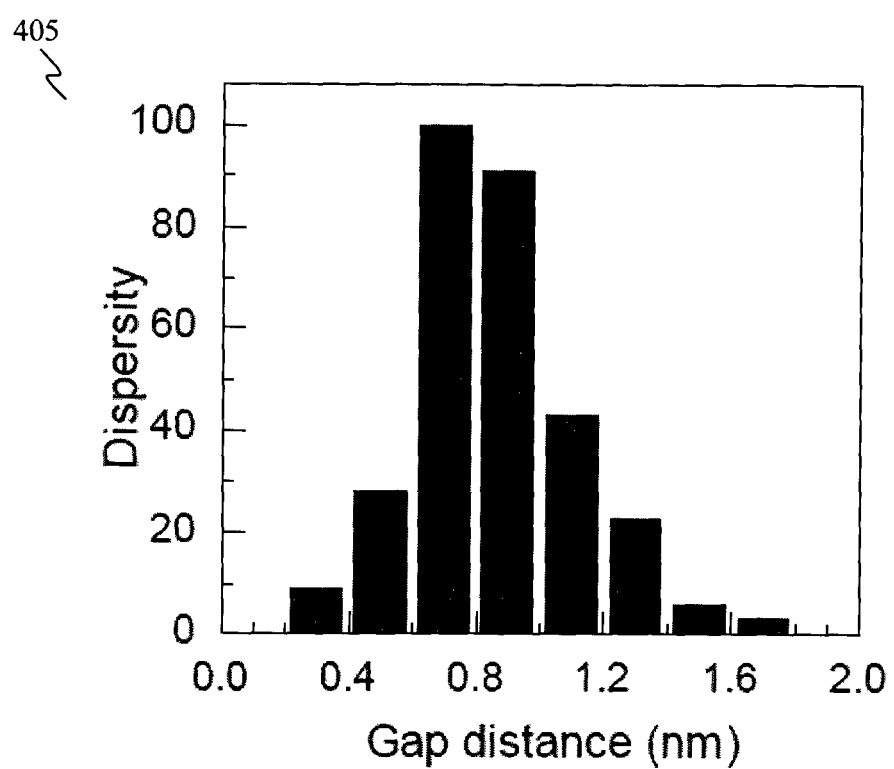
FIG. 4E shows a plot of distribution of the edge-to-edge spacing of gold (Au) nanorods after an ultraviolet (UV) ozone treatment.

In order to change the gap distance, h, between adjacent Au nanorods, the CTAB molecules attached on the nanorod surface during synthesis of the Au nanorods may be removed. In various embodiments, the CTAB molecules may be at least substantially removed by means of an ultraviolet (UV) ozone treatment. In a non-limiting example, a vertical Au nanorod monolayer array, on a substrate, with approximately 7.7 nm gap distance was treated with a UV ozone cleaning. Surprisingly, the inventors found that the edge-to-edge spacing or gap distance, h, between adjacent Au nanorods sharply decreases to sub-nm of approximately 0.8±0.3 nm, and crack patterns are formed, as may be observed from the SEM images 403 (FIG. 4C), 404 (FIG. 4D) illustrating the same region of the array of vertical Au nanorods before and after treatment by UV ozone, respectively. The respective scale bars in FIGS. 4C and 4D represent 100 nm. FIG. 4E shows a plot 405 of distribution of the edge-to-edge gap distance, h, of gold (Au) nanorods after the ultraviolet (UV) ozone treatment. As may be observed, the edge-to-edge gap distance, h, is predominantly distributed between about 0.6 nm and about 1.0 nm. The decrease in the edge-to-edge gap distance or separation, h, may be because the electrostatic repulsive force between Au nanorods diminishes as the CTAB molecules are removed from the surface of the Au nanorods. The van der Waals forces in turn may further drag the nanorods closer to each other. This may lead to the crack pattern and sub-nm gap distance formation in each domain. As a result of the decrease in the edge-to-edge gap distance, h, the local electromagnetic enhancement may be dramatically improved upon UV ozone treatment, which in is line with the results shown in plot 107 of FIG. 1E.

Figure 5A:
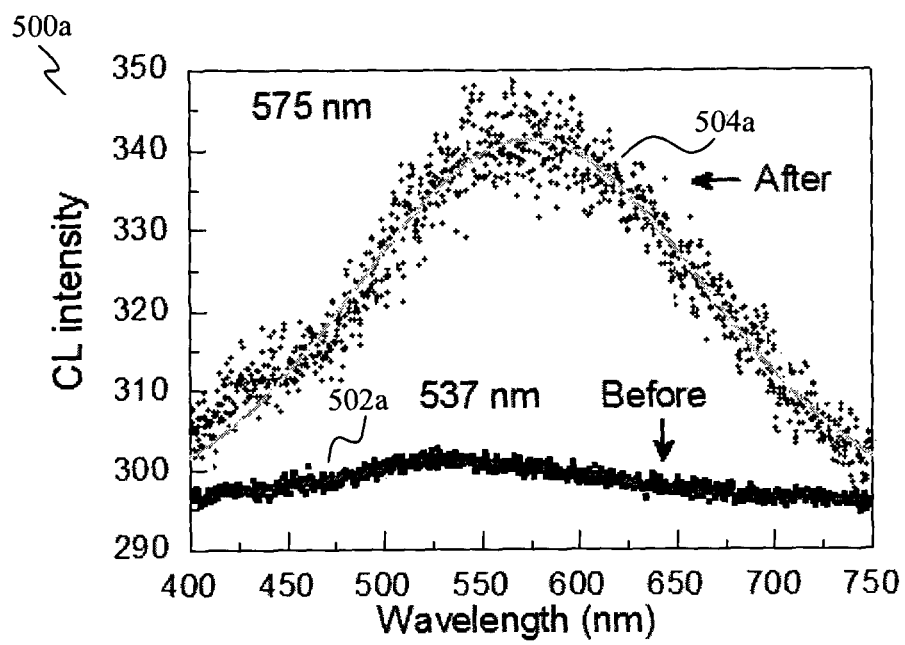
FIG. 5A shows a plot of cathodoluminescence (CL) spectra of a vertically aligned gold (Au) nanorod monolayer before and after treatment by UV ozone.
Figure 5B:
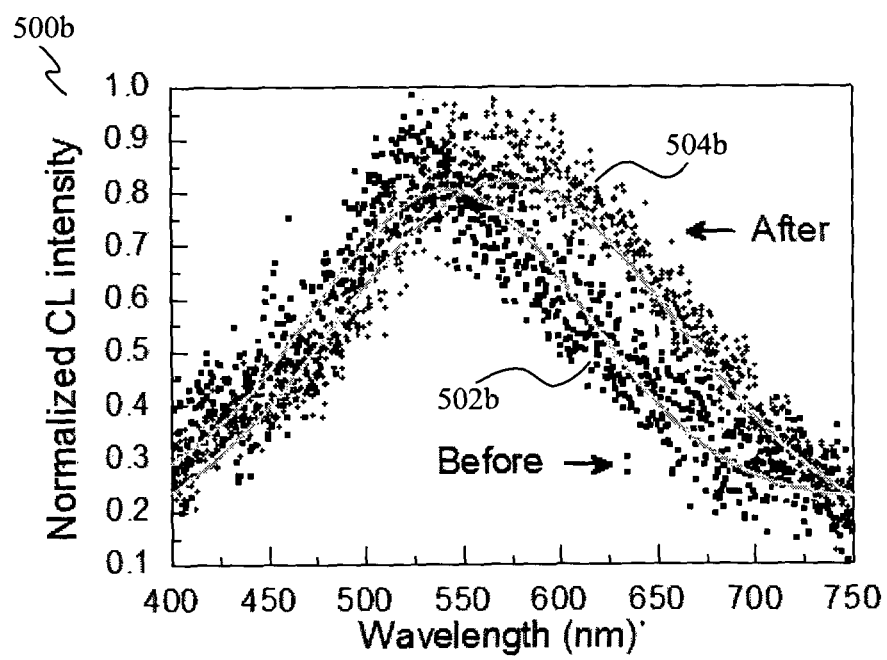
FIG. 5B shows a plot of normalised cathodoluminescence (CL) spectra based on the cathodoluminescence (CL) spectra of FIG. 5A.

In order to better understand the decrease of the gap size, h, between adjacent Au nanorods, a cathodoluminescence (CL) system may be used to investigate the plasmon response of the Au nanorods, which may be excited by a focused 8 kV electron beam. FIG. 5A shows a plot 500a of cathodoluminescence (CL) specta of the vertically aligned gold (Au) nanorod monolayer before and after treatment by UV ozone, while FIG. 5B shows a plot 500b of normalised cathodoluminescence (CL) specta based on the CL spectra of FIG. 5A. The CL spectra prior to the UV ozone treatment are represented by the results 502a (FIG. 5A), 502b (FIG. 5B), while CL spectra obtained after the UV ozone treatment are represented by the results 504a (FIG. 5A), 504b (FIG. 5B).

As may be observed in FIGS. 5A and 5B, after the treatment by UV ozone, the CL spectra show a red-shift from about 537 nm to about 575 nm, indicating a decrease in the gap size or separation, h, between the Au nanorods. Further, the CL intensity increases sharply after the UV ozone treatment, which indicates that the plasmon coupling is enhanced, further verifying the decrease in the gap size.

Highly organized vertical monolayer arrays of Au nanorods may be obtained or formed on a variety of substrates, ranging from indium tin oxide (ITO)-covered glass, gallium nitride (GaN) light emitting diode (LED) device, glass substrates, to even flexible poly(ethylene naphthalate) (PEN) films.

Figure 6A:
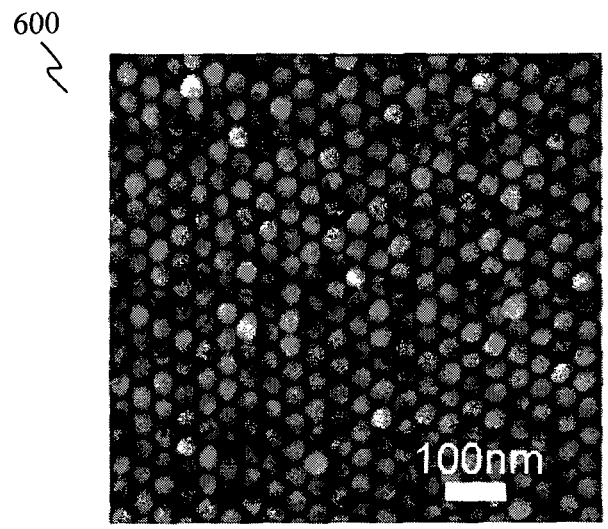
FIG. 6A shows a scanning electron microscopy (SEM) image of an array of vertical gold (Au) nanorods on a gallium nitride (GaN) light emitting diode (LED) device.
Figure 6B:
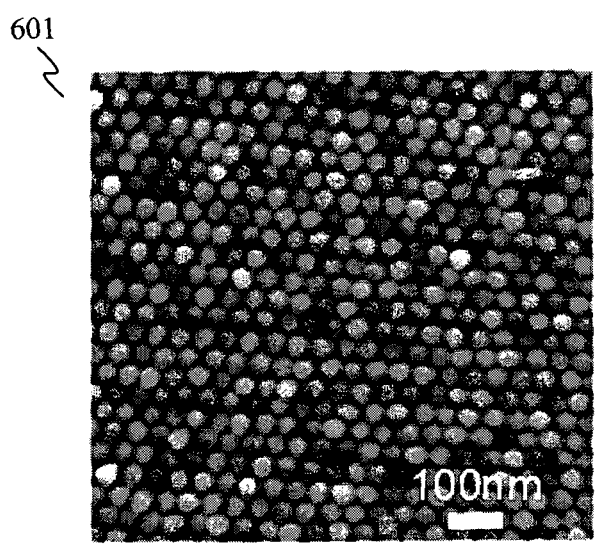
FIG. 6B shows a scanning electron microscopy (SEM) image of an array of vertical gold (Au) nanorods on an indium tin oxide (ITO)-coated glass.
Figure 6C:
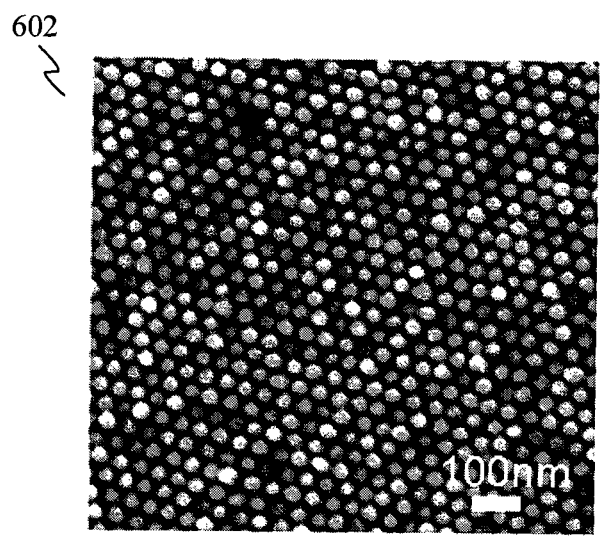
FIG. 6C shows a scanning electron microscopy (SEM) image of an array of vertical gold (Au) nanorods on a glass.
Figure 6D:
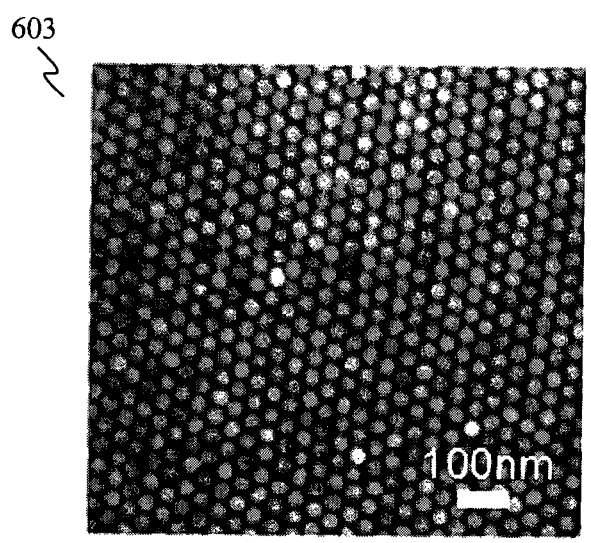
FIG. 6D shows a scanning electron microscopy (SEM) image of an array of vertical gold (Au) nanorods on a flexible poly(ethylene naphthalate) (PEN) polymer film.
Figure 6E:
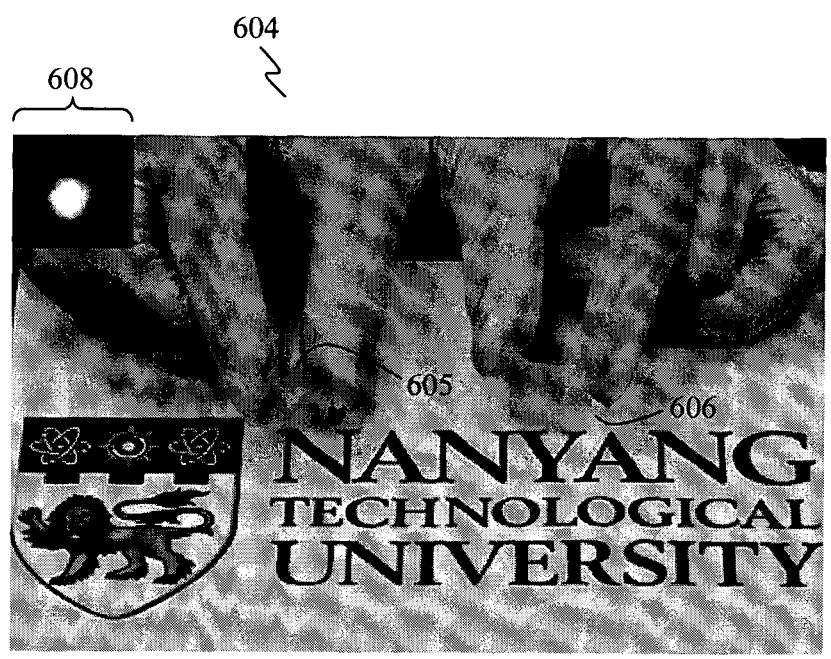
FIG. 6E shows a photograph of respective arrangements of arrays of vertical Au nanorods on a gallium nitride (GaN) light emitting diode (LED) device and a flexible poly(ethylene naphthalate) (PEN) film.

FIG. 6A shows a scanning electron microscopy (SEM) image 600 of an array of vertical gold (Au) nanorods on a gallium nitride (GaN) light emitting diode (LED) device. FIG. 6B shows a scanning electron microscopy (SEM) image 601 of an array of vertical gold (Au) nanorods on an indium tin oxide (ITO) coating of an ITO glass. FIG. 6C shows a scanning electron microscopy (SEM) image 602 of an array of vertical gold (Au) nanorods on a glass. FIG. 6D shows a scanning electron microscopy (SEM) image 603 of an array of vertical gold (Au) nanorods on a flexible poly (ethylene naphthalate) (PEN) polymer film. The respective scale bar in FIGS. 6A to 6D represents 100 nm. FIG. 6E shows a photograph 604 of an arrangement 605 of an array of vertical Au nanorods on a GaN LED device and an arrangement 606 of an array of vertical Au nanorods on a flexible PEN film. As may be observed, the arrangement 606 may be urged into a curve, illustrating its flexibility. The inset in FIG. 6E shows a photograph 608 of the GaN LED device at about 3.5 mA current.

Accordingly, various embodiments of the monolayer array of vertically aligned Au nanorods on a substrate may be of high interest for a wide range of potential applications, such as, for example, for control of the directionality and polarization of LEDs, and as a light enhancer in flexible electronic and photonic devices. The results also indicate that the formation of vertically aligned monolayer is independent of the substrates used.

Figure 7A:
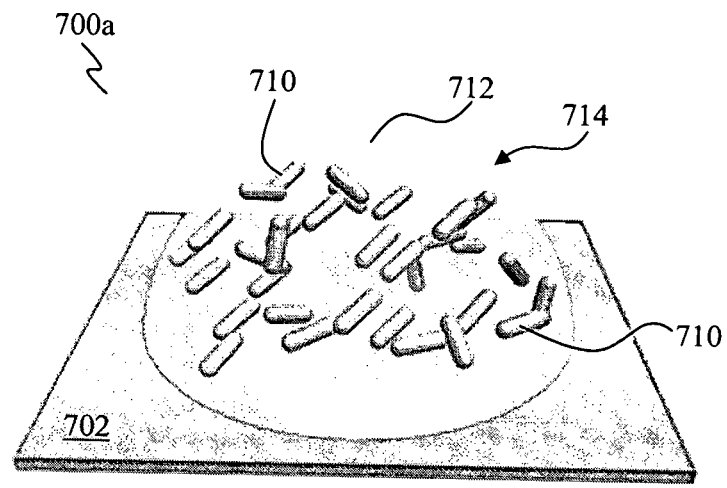
FIGS. 7A to 7C show a schematic representation of the evolution of vertical gold (Au) nanorod self-assembly arrays in different stages of the process.
Figure 7B:
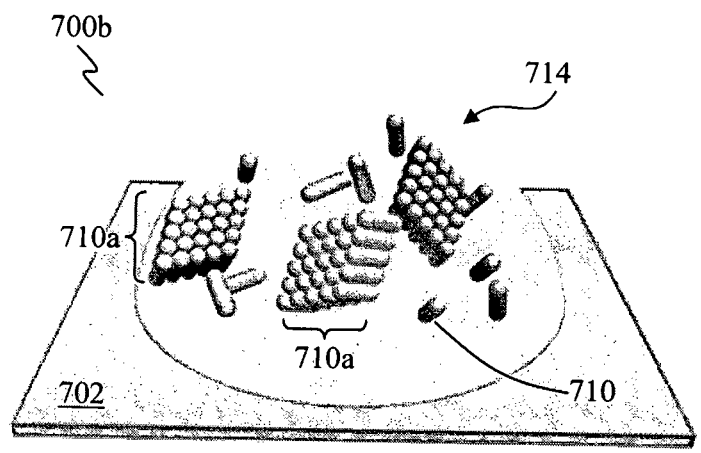
Figure 7C:
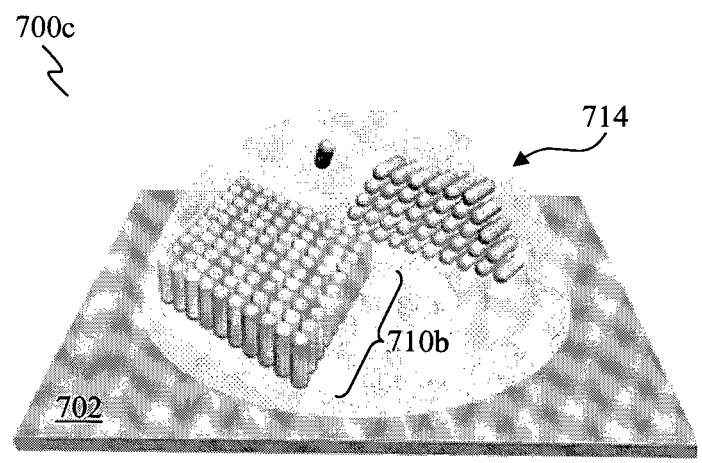

While not wishing to be bound, the following may be one example of a mechanism of the self-assembly of the Au nanorods on a substrate. FIGS. 7A to 7C show a schematic representation of the evolution of vertical gold (Au) nanorod self-assembly arrays in different stages of the process. Gold (Au) nanorods may be dispersed in a NaCl aqueous solution to form a solution, in which a droplet of the solution may then be provided on a substrate. FIG. 7A shows a schematic diagram 700a of the initial dispersion of gold (Au) nanorods 710 in a NaCl aqueous solution 712, in the form of a droplet 714, on a substrate 702. The Au nanorods 710 in the aqueous dispersion or solution may form an initial hexagonal nucleus in a side-to-side model, and then free Au nanorods 710 may assemble around the nucleus, leading to the growth of hexagonal monolayer arrays 710a, as shown in the schematic diagram 700b of FIG. 7B illustrating the nucleation and growth process of the self-assemblies of the Au nanorods 710. The monolayer arrays 710a may then precipitate to stand up on the substrate 702 due to gravity and van der Waal's interactions to the host substrate 702. FIG. 7C shows a schematic diagram 700c of the sedimentation and the final formation of the Au nanorod vertical arrays 710b.

Figure 8:
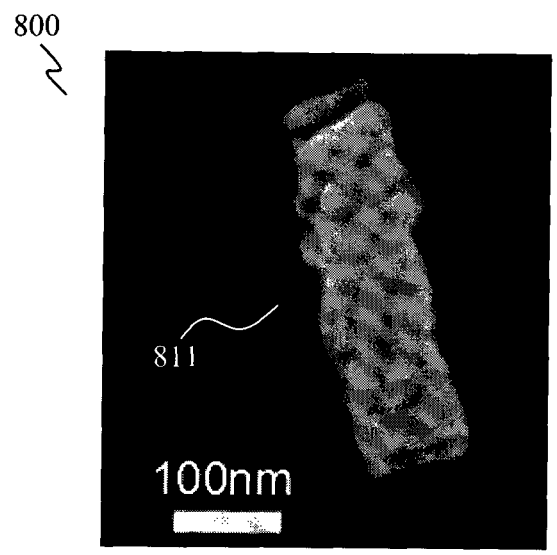
FIG. 8 shows a scanning electron microscopy (SEM) image of a monolayer gold (Au) nanorod array lying down on a substrate horizontally.

A few monolayer arrays of Au nanorods may be observed lying down on the substrate horizontally after formation. FIG. 8 shows a scanning electron microscopy (SEM) image 800 of a monolayer gold (Au) nanorod array 811 lying down on a substrate horizontally. However, the small number of Au nanorod arrays lying horizontally on the substrate provides support for the mechanism described above. The vertical monolayer array predominates because it has a larger contact area with respect to the substrate and is subjected to minimization of surface energy.

During the self-assembly process, the van der Waals force and the attractive depletion force may induce adjacent Au nanorods to approach each other. An electrostatic repulsive force may be responsible for stabilizing the Au nanorods within a certain distance and may prevent them from random aggregation. The synergy between the attractive and repulsive forces may induce the Au nanorods to form highly ordered phases.

In order to determine the electrostatic energy between two similar parallel rods, the Derjaguin's approximation may be used, which assumes that the parallel rods may be considered to be formed by contributions of two parallel thin plates. The electrostatic interaction energy per unit area between two similar parallel plates, $E_{pl}$, may be written as $$E_{pl} = \varepsilon\varepsilon_0\kappa\varphi^2\left[1 - \tanh\left(\kappa\frac{h - 2t_{CTAB}}{2}\right)\right], \quad \text{(Equation 2)}$$

where $\varepsilon$ and $\varepsilon_0$ are the relative electric permittivity of the electrolyte solution and the electric permittivity of a vacuum, respectively, $\kappa$ is the inverse Debye length, $\varphi$ is the Zeta potential of Au rods, h is the edge-to-edge spacing between the plates, and $t_{CTAB}$ is the thickness of the CTAB bilayer on the surface of the plate, which is about 3.2 nm.

With the help of the Derjaguin's approximation, the electrostatic energy between two similar parallel rods, $E_{ele}$, may be given by $$E_{ele} = l\int_{-\infty}^{\infty} E_{pl}dx = 2l\sqrt{\pi\kappa r}\,\varepsilon\varepsilon_0\varphi^2 Li_{1/2}(-e^{-\kappa(h-2t_{CTAB})}), \quad \text{(Equation 3)}$$

where l is the length of the Au rod, r is the radius of the Au rod, $\kappa r \gg 1$ and $(h-2t_{CTAB}) \ll r$, and $Li_s(x)$ is a polylogarithm function, defined by $$Li_s(x) = \sum_{k=1}^{\infty} \frac{x^k}{k^s}.$$

As an example, the van der Waals potential, $E_{vdw}$, the depletion potential, $E_{dep}$, and the electrostatic energy, $E_{ele}$, as a function of separation, h, may be calculated, as illustrated below, in the case of the Debye length, $\kappa^{-1}$, of about 3.0 nm. The van der Waals potential, $E_{vdw}$, of two similar parallel rods may be given by $$E_{Vdw} = -\frac{Alr^{1/2}}{24h^{3/2}}, \quad \text{(Equation 4)}$$

where A is the effective Hamaker constant (~1×10⁻¹⁹ J), l is the length of the Au rod, r is is the radius of the Au rod, and h is the separation between the surfaces of adjacent Au rods.

The depletion potential, $E_{dep}$, between two parallel Au nanorods may be given by $$E_{dep} = -\frac{1}{2}lP_0\left[-h\sqrt{(2r+m)^3 - h^2} + (2r+m)^2\arccos\left(\frac{h}{2r+m}\right)\right],$$ (Equation 5)

where m is the diameter of CTAB micelles (5.8 nm), $P_0 = n_{micelles}R_cT$ is the osmotic pressure generated by the micelles, $R_c$ is the universal gas constant, T is the temperature in Kelvin degree, $n_{micelles}$ is the concentration of CTAB micelles ($n_{micelles}=(c_{CTAB}-c_{CMC})/N_{agg}$, where $N_{agg}$ is the aggregation number of CTAB micelles (120, 2.5 mM), $c_{CTAB}$ is the concentration of CTAB, and $c_{CMC}$ is the critical micelle concentration of CTAB (0.92 mM)).

Figure 9A:
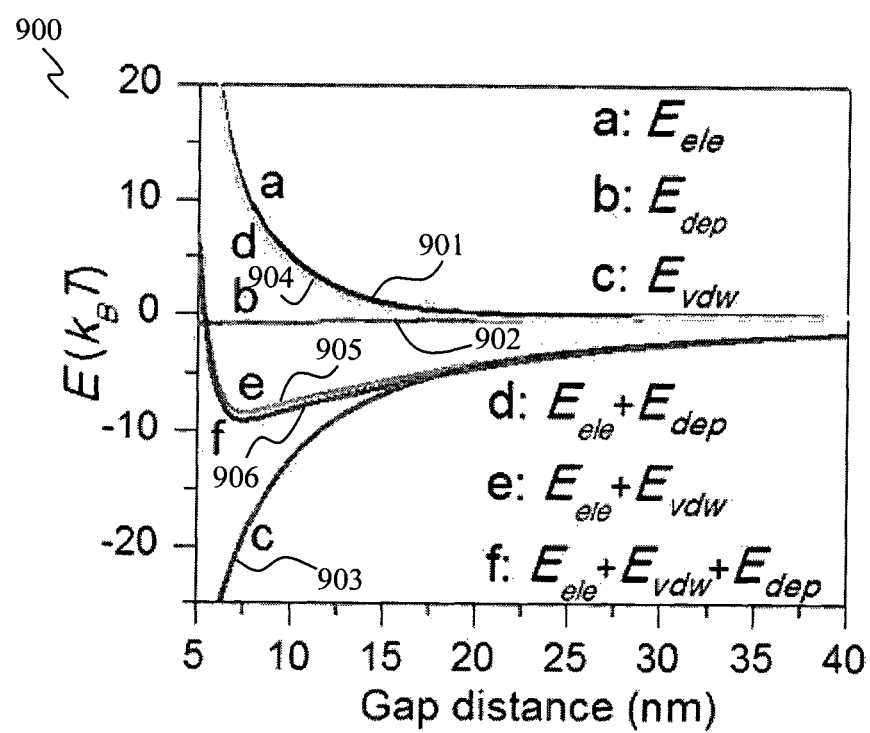
FIG. 9A shows a plot of interaction free energy as a function of separation between two gold (Au) nanorods when the Debye length, $\kappa^{-1}$, is about 3 nm.
Figure 9B:
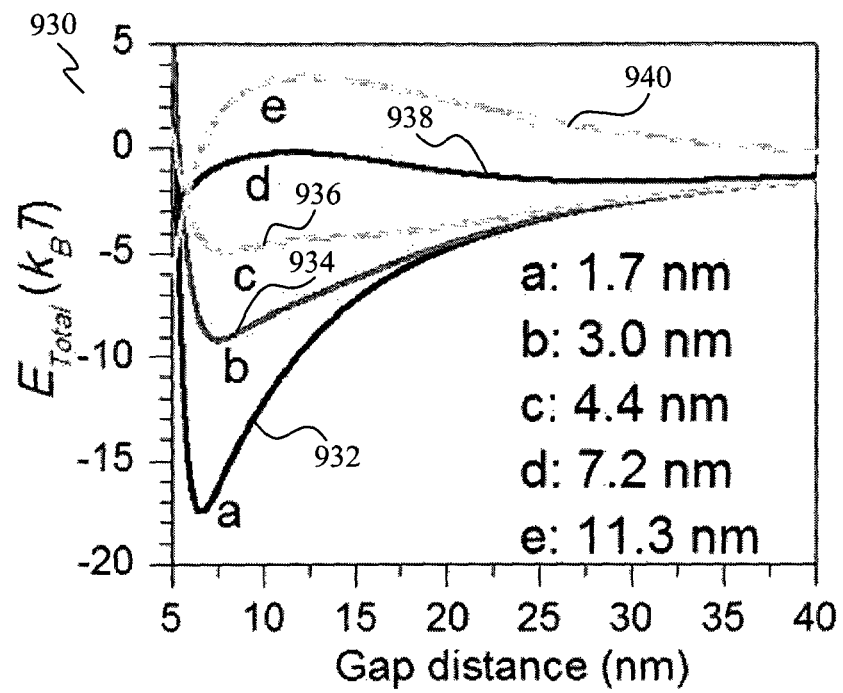
FIG. 9B shows a plot of total interaction energy, $E_{Total}$, as a function of separation between two parallel gold (Au) nanorods for different Debye lengths.

FIGS. 9A and 9B show the theoretical calculation results for the self-assemblies of Au nanorods. FIG. 9A shows a plot 900 of interaction free energy as a function of separation (or gap distance), h, between two gold (Au) nanorods when the Debye length, $\kappa^{-1}$, is about 3 nm. Plot 900 shows result 901 for $E_{ele}$, result 902 for $E_{dep}$, result 903 for $E_{vdw}$, result 904 for the sum of $E_{ele}$ and $E_{dep}$ (i.e. $E_{ele}+E_{dep}$), result 905 for the sum of $E_{ele}$ and $E_{vdw}$ (i.e. $E_{ele}+E_{vdw}$), and result 906 for the sum of $E_{ele}$, $E_{vdw}$ and $E_{dep}$ (i.e. $E_{ele}+E_{vdw}+E_{dep}$).

The depletion interaction, $E_{dep}$, is much smaller than the van der Waals, $E_{vdw}$, and the electrostatic, $E_{ele}$, interactions. If only the electrostatic and the depletion interactions are considered, the resultant force may still be repulsive. However, the synergy of the electrostatic and the van der Waals interactions may result in the energy being minimized at a separation of about 7.5 nm, which is in good agreement with the experimental data of about 7.7 nm. Therefore, the electrostatic interaction, $E_{ele}$, and the van der Waals interaction, $E_{vdw}$, may be predominant for the formation of vertical arrays of Au nanorods. The total interaction energy, $E_{Total}$, defined by $E_{Total}=E_{ele}+E_{dep}+E_{vdw}$, as a function of separation (gap distance), h, between two parallel similar Au nanorods may be as shown in FIG. 9B. FIG. 9B shows a plot 930 of total interaction energy, $E_{Total}$, as a function of separation (or gap distance), h, between two parallel gold (Au) nanorods for different Debye lengths, $\kappa^{-1}$. Plot 930 shows result 932 for $\kappa^{-1}=1.7$ nm, result 934 for $\kappa^{-1}=3.0$ nm, result 936 for $\kappa^{-1}=4.4$ nm, result 938 for $\kappa^{-1}=7.2$ nm, and result 940 for $\kappa^{-1}=11.3$ nm.

The free energy may be minimized at a separation, h, of about 6.6 nm, about 7.5 nm, and about 7.8 nm when the Debye length is about 1.7 nm, about 3.0 nm, and about 4.4 nm, respectively, which are in good agreement with the experimental data. Further, the minimum in the interaction energy becomes deeper and the separation between two Au nanorods decreases as the Debye length decreases. However, when the Debye length is about 7.2 nm and about 11.3 nm, Equation 3 may no longer be applicable because the corresponding values of κr are about 2.4 and about 1.5, respectively, which are close to 1. The free energy when the Debye lengths are about 7.2 nm and about 11.3 nm is maximized at about 10.6 nm and about 11.8 nm, respectively, suggesting that it may not be possible to assemble nanorods in a vertical monolayer array under such ionic strengths.

Detection of plasticizers (e.g. phthalates) and melamine using various embodiments of the array of vertically aligned Au nanorods on a substrate will now be described by way of the following non-limiting examples. The vertical monolayer arrays of Au nanorods may be exploited for ultrasensitive detection of food contaminants such as plasticizers and melamine. Phthalate is known as an endocrine disrupter which produces reproductive and developmental toxicity, which may cause issues such as miscarriage, fewer motile sperm and external sex organs malformation in infants. Melamine, known as a triazine heterocyclic organic chemical material, can block and damage renal cells, resulting in kidney malfunction, and even death in infants.

A highly aligned vertical monolayer of Au nanorods with approximately 7.7 nm edge-to-edge gap, h, was used as the SERS substrate and Benzylbutylphthalate (BBP, $C_{19}H_{20}O_4$) was used to determine quantitatively the SERS signal. The Raman scattering spectroscopy was conducted with a 785 nm excitation source. In order to eliminate or at least minimise any signal interference due to the CTAB molecules that were absorbed on the surface of the Au nanorods during the synthesis process, the vertical Au nanorod monolayer array was treated with UV ozone cleaning so as to remove the CTAB molecules. The UV ozone treatment was carried out for about 20 minutes without heating. In this way, a highly aligned vertical monolayer of Au nanorods with approximately 0.8 nm edge-to-edge gap distance, h, may be obtained after the UV ozone treatment.

Plasticizer ethanol solutions and melamine methanol solutions, such as Benzylbutylphthalate (BBP, $C_{19}H_{20}O_4$), Dibutyl phthalate (DBP, $C_{16}H_{22}O_4$), Diethyl Phthalate (DEP, $C_{12}H_{14}O_4$), Bis(2-ethylhexyl)phthalate (DEHP, $C_{24}H_{38}O_4$), were prepared with different concentrations, e.g. about 1 fM, 1 pM, and 1 nM. For BBP detection, approximately 10 μL BBP ethanol solution (1 fM) was dropped onto an array of vertical Au nanorods on a 1×1 cm² silicon (Si) substrate, which spread quickly. After about 1 hour, ethanol totally evaporated, and SERS signals were recorded. For other plasticizers and melamine, the procedure used was the same.

Figure 10A:
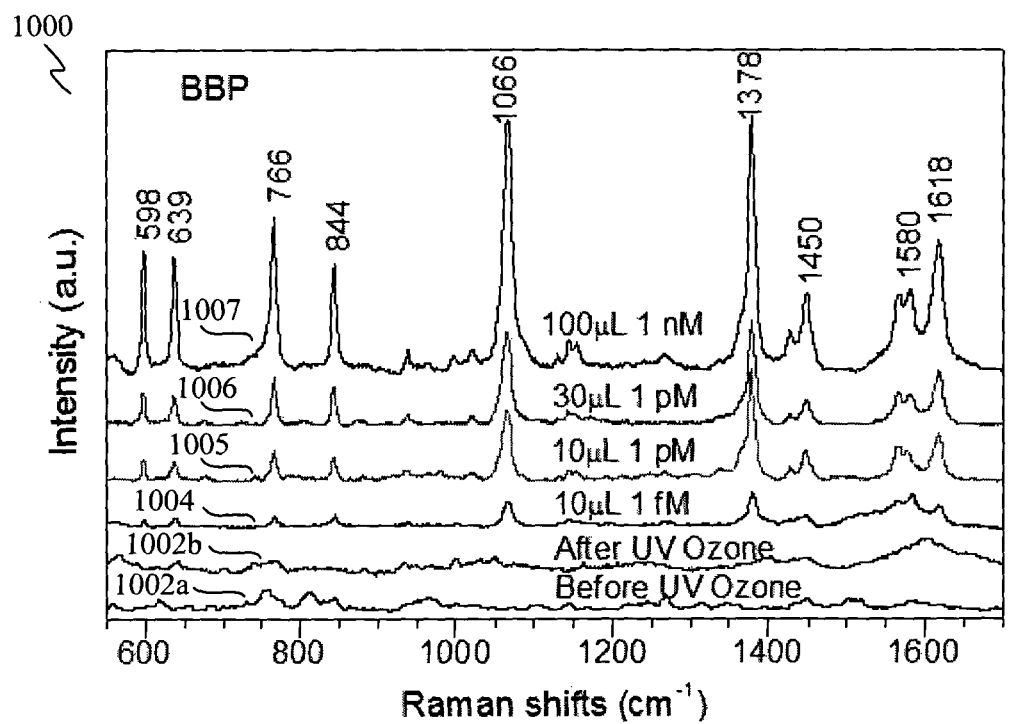
FIG. 10A shows a plot of surface enhanced Raman scattering (SERS) spectra of Benzylbutylphthalate (BBP) on a vertically-aligned monolayer gold (Au) nanorod array.

FIG. 10A shows a plot 1000 of surface enhanced Raman scattering (SERS) spectra of Benzylbutylphthalate (BBP) on a vertically-aligned monolayer Au nanorod array. Plot 1000 shows a SERS spectrum 1002a and a SERS spectrum 1002b for the array of Au nanorods prior to and post UV ozone treatment, respectively. As may be observed, the characteristic peaks of CTAB molecules at about 755 cm⁻¹ (—C—N⁺ stretching vibration), about 844 cm⁻¹ (CH₃ deformation), about 1144 cm⁻¹ (C—C stretching vibration), and about 1266 cm⁻¹ (CH₂ wagging vibration) disappear after the UV ozone treatment, when compared to the Raman spectrum of the CTAB molecules before the UV ozone treatment, as shown by the spectrum 1002a, which further verifies that CTAB molecules were wiped out or removed completely from the surface of the Au nanorods.

Plot 1000 further shows a SERS spectrum 1004 corresponding to about 10 μL, 1 fM BBP, a SERS spectrum 1005 corresponding to about 10 μL, 1 pM BBP, a SERS spectrum 1006 corresponding to about 30 μL, 1 pM BBP, and a SERS spectrum 1007 corresponding to about 100 μL, 1 nM BBP. As illustrated in FIG. 10A, when approximately 10 μL solution of BBP (1 fM) in ethanol was drop-casted on the vertical Au rods monolayer array standing on approximately 1×1 cm² Si substrate, a pronounced Raman signal may be observed from the spectrum 1004. As the concentration and volume of the BBP solution increase, the overall spectral intensity is rather quantitatively increased, with similar spectral features, as may be observed from spectra 1004, 1005, 1006, 1007. The Raman peaks at about 1066 cm⁻¹, about 1580 cm$^{-1}$, and about 1618 cm$^{-1}$ correspond to the ring-ring stretching vibration of ortho-phenyl group, and the peaks at about 598 cm$^{-1}$, about 639 cm$^{-1}$, and about 766, cm$^{-1}$ are due to ring deformation. The peaks at about 844 cm$^{-1}$, about 1378 cm$^{-1}$, and about 1450 cm$^{-1}$ may be assigned to the aromatic C—H twisting vibration, the CH$_3$ symmetric deformation, and the C—H in plane bending of alkyl group, respectively.

Figure 10B:
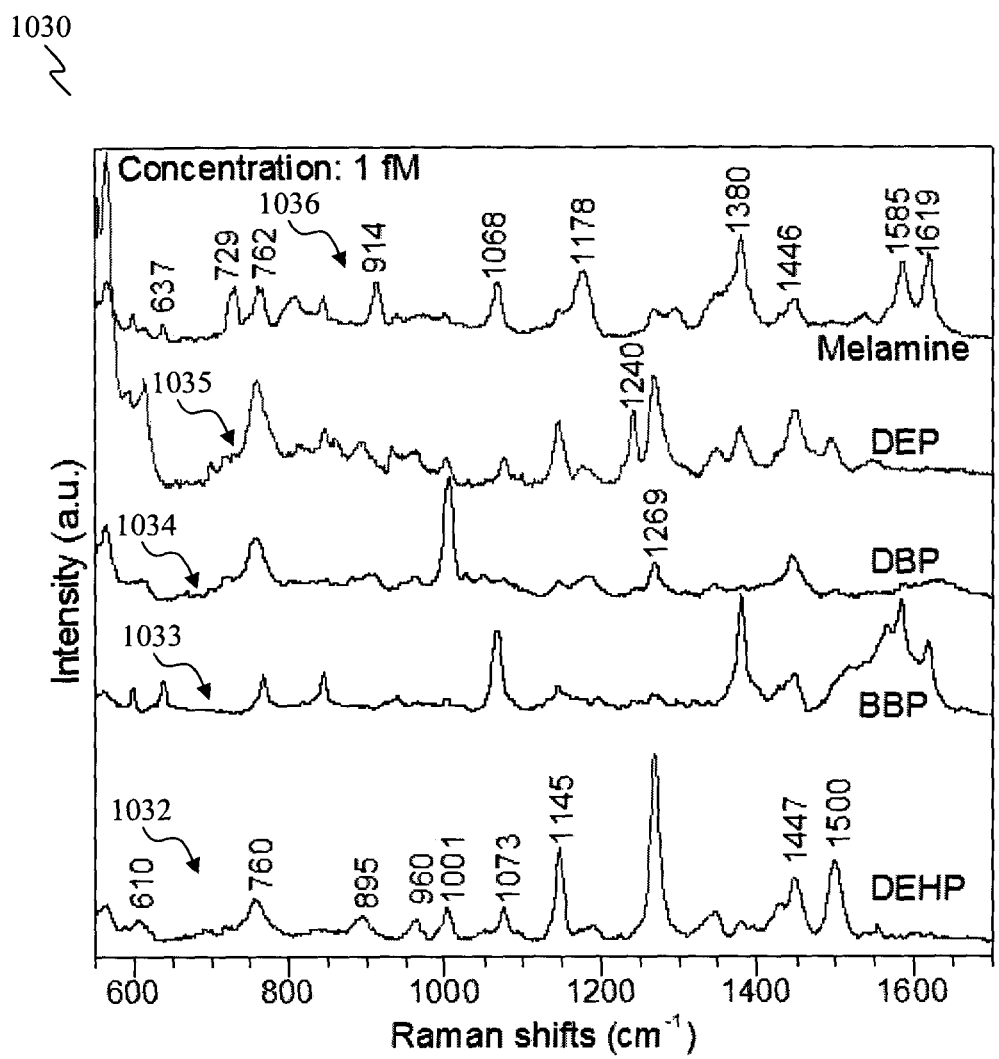
FIG. 10B shows a plot of surface enhanced Raman scattering (SERS) spectra of plasticizers and melamine, at a concentration of about 1 fM, on a vertically-aligned monolayer gold (Au) nanorod array.

Based on the highly sensitive SERS substrates of various embodiments, melamine ($C_3H_6N_6$) and other plasticizers at a femtomolar level, such as Bis(2-ethylhexyl)phthalate (DEHP, $C_{24}H_{38}O_4$), Dibutyl phthalate (DBP, $C_{16}H_{22}O_4$), and Diethyl Phthalate (DEP, $C_{12}H_{14}O_4$), may also be detected. FIG. 10B shows a plot 1030 of surface enhanced Raman scattering (SERS) spectra of plasticizers and melamine, at a concentration of about 1 fM, on a vertically-aligned monolayer Au nanorod array.

Plot 1030 shows a SERS spectrum 1032 corresponding to about 20 μL, 1 fM DEHP, a SERS spectrum 1033 corresponding to about 10 μL, 1 fM BBP, a SERS spectrum 1034 corresponding to about 20 μL, 1 fM DBP, a SERS spectrum 1035 corresponding to about 20 μL, 1 fM DEP, and a SERS spectrum 1036 corresponding to about 10 μL, 1 fM melamine. The spectrum 1033 corresponds to the spectrum 1004 of FIG. 10A, but in an expanded view.

For melamine, the peaks at about 637 cm$^{-1}$ and about 914 cm$^{-1}$ may be assigned to the ring breathing mode, involving an in-plane deformation of the triazine ring. The peaks at about 729 cm$^{-1}$ and about 762 cm$^{-1}$ correspond to the out-of-plane vibration of the ring. The ring stretching vibration are at about 1068 cm$^{-1}$, and about 1178 cm$^{-1}$. The range of 1350-1450 cm$^{-1}$ may be assigned to the semi-circle ring stretch. The quadrant ring stretching vibrations may be in the 1500-1600 cm$^{-1}$ region. The peak at about 1620 cm$^{-1}$ is from NH$_2$ deformation.

Such a femtomolar (fM) level sensitivity and molecular fingerprint identification suggest that the vertical Au nanorod arrays of various embodiments may pave the way for direct and fast detection of food contaminants in the real world, such as in food or drinks.

Plasticizer (e.g. BBP and DEHP) detection in orange juice samples were carried out to detect trace amounts of BBP and DEHP (0.9 fM) in orange juices. Approximately 10 μL orange juice sample was extracted from a bottle of a commercial brand orange juice available in Singapore. The orange juice sample was mixed with a phthalate plasticizer (BBP or DEHP) ethanol solution (approximately 90 μL, 1 fM), so that the actual BBP or DEHP concentration is about 0.9 fM. Besides water, pure orange juice mainly contains Vitamin C and carotene. Approximately 10 μL mixture solution of the orange juice sample containing either BBP or DEHP was drop-casted onto a vertical array of Au nanorods on a 1×1 cm$^2$ Si substrate. After the ethanol has completely evaporated, SERS signals were recorded.

Figure 10C:
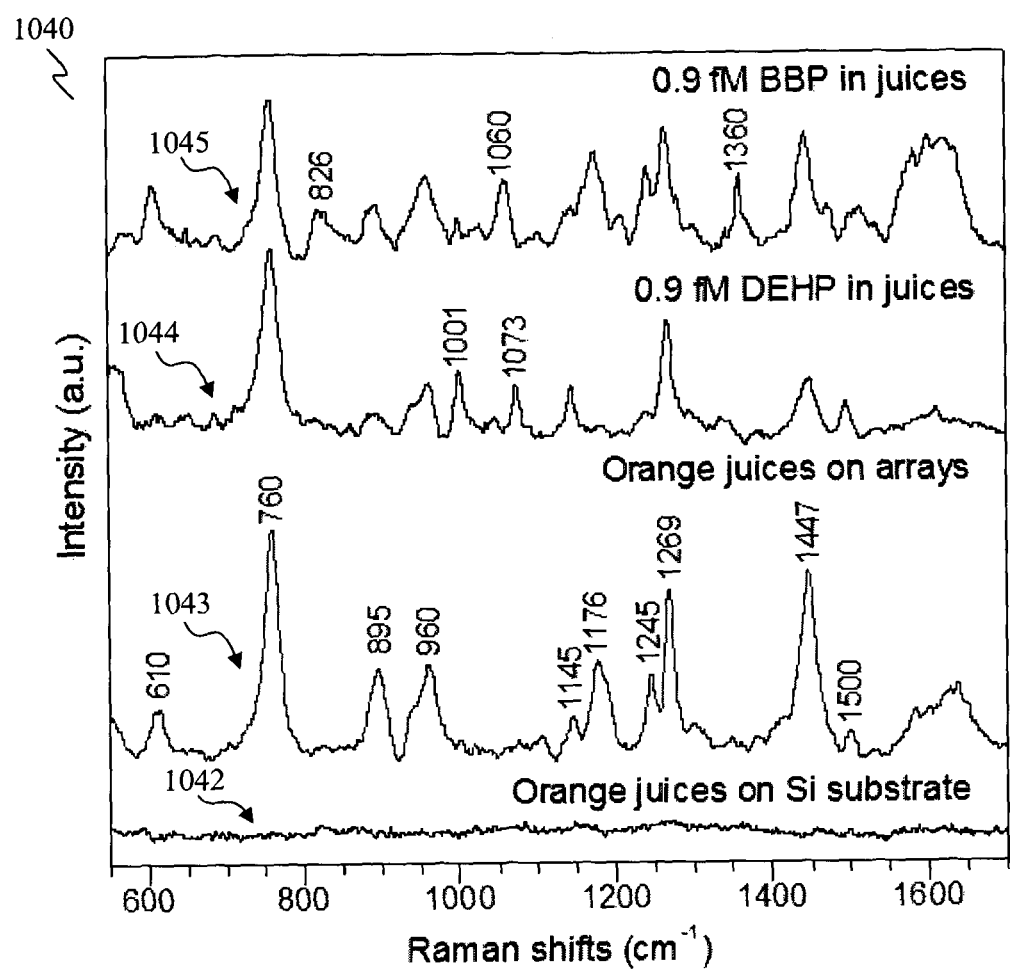
FIG. 10C shows a plot of surface enhanced Raman scattering (SERS) spectra for detection of Benzylbutylphthalate (BBP) and Bis(2-ethylhexyl)phthalate (DEHP) at a femtomolar level (fM) in orange juices on a vertically-aligned monolayer gold (Au) nanorod array.

FIG. 10C shows a plot 1040 of surface enhanced Raman scattering (SERS) spectra for detection of Benzylbutyl-phthalate (BBP) and Bis(2-ethylhexyl)phthalate (DEHP) at a femtomolar level (fM) in orange juices on a vertically-aligned monolayer Au nanorod array. Plot 1040 shows a SERS spectrum 1042 corresponding to an orange juice on a Si substrate, a SERS spectrum 1043 corresponding to about 10 μL mixture solution of orange juice and ethanol, a SERS spectrum 1044 corresponding to about 10 μL, 0.9 fM DEHP in a mixture solution containing orange juice and ethanol, and a SERS spectrum 1045 corresponding to about 10 μL, 0.9 fM BBP in a mixture solution containing orange juice and ethanol.

Direct Raman analysis of pure orange juice on a Si substrate does not offer any detectable Raman signals, as shown by the spectrum 1042. However, the SERS spectrum 1043 of the orange juice taken on a vertical Au nanorod array shows the fingerprint features of Vitamin C and carotene at about 610 cm$^{-1}$ (C—C ring stretching), about 760 cm$^{-1}$ (OH out-of-plane deformation), about 895 cm$^{-1}$ (C—C ring stretching), about 960 cm$^{-1}$ (C—H and O—H in plane bending), about 1145 cm$^{-1}$ (C—O—C stretching), about 1176 cm$^{-1}$ (Methyl rock), about 1245 cm$^{-1}$ (C—O—H bending), about 1269 cm$^{-1}$ (C—O—C stretching), about 1447 cm$^{-1}$ (C—H scissoring), and about 1500 cm$^{-1}$ (C=C stretching), with the corresponding vibrational modes or peaks identified in FIG. 10C.

After addition of DEHP in orange juice at about 0.9 fM, the Raman peaks of DEHP at about 1001 cm$^{-1}$ and about 1073 cm$^{-1}$, which may be assigned to the ring-ring stretching mode, may be detected as shown by the spectrum 1044 as compared to the SERS spectrum 1043 of orange juice. For the BBP contaminated orange juice, the Raman peaks of BBP at about 826 cm$^{-1}$, about 1060 cm$^{-1}$ and about 1360 cm$^{-1}$ may be clearly identified in the spectrum 1045, although a few wavenumber red shift (i.e. a shift to lower energy) may be observed in comparison to the spectra of the BBP molecules in ethanol as shown in FIG. 10A, which may be due to the intermolecular interactions between BBP molecules and Vitamin C in juices by hydrogen bond and π-electrons. BBP and DEHP may be distinguished unambiguously, although they may share some similar Raman fingerprints. The results indicate that plasticizer contaminations in actual orange juice samples may be detected at a femtomolar level, suggesting great potential of nanorod monolayer for real applications in food safety and environmental screening.

It should be appreciated that the Au nanorod monolayer on substrate is not confined to detection of food contaminants, but may be employed to detect any organic compounds in general.

As described above, various embodiments may provide an evaporation-induced self-assembly of CTAB-coated Au nanorods to form highly organized vertical monolayer arrays, which may be reproducibly prepared on arbitrary substrates, such as but not limited to silicon (Si), glass, gallium nitride light emitting diode (GaN LED) and flexible poly(ethylene naphthalate) (PEN) polymer. The edge-to-edge spacing or separation, h, between adjacent Au nanorods may be tuned between about 11.8 nm and about 6.7 nm by adjusting the ionic strength of the solution containing the Au nanorods. The synergy between the electrostatic repulsive force and the van der Waals attractive force may maintain the Au nanorod arrays at an equilibrium status. The decrease of electrostatic force may induce the Au nanorods to approach each other in an ambient environment, which may result in a smaller edge-to-edge gap distance, h. For example, the gap distance, h, may be decreased to a sub-nm regime, for example 0.8±0.3 nm, from an array of Au nanorods on a substrate having an edge-to-edge separation, h, of about 7.7 nm, by removing the CTAB molecules absorbed on the Au nanorods by an ultraviolet (UV) ozone treatment.

Finite-difference time-domain method (FDTD) calculation shows that the vertical monolayer arrays may exhibit a strong and uniform electric field enhancement in the gaps between adjacent nanorods in the order of about 10$^6$ at the sub-nm gap distance, which may result in an exceptional femtomolar detection of a variety of plasticizers in surface enhanced Raman scattering (SERS) with molecular fingerprint clearly resolved.

Various embodiments may provide a simple but robust approach to self-assemble CTAB (hexadecyltrimethylammonium bromide)-coated Au nanorods into vertical monolayer arrays. Based on the vertical-aligned Au nanorod monolayer, food contaminants such as plasticizers and melamine may be detected at a femtomolar (fM) level, which is about 7 orders of magnitude lower than the maximum allowable level of approximately 6 ppb regulated by the U.S. Food and Drug Administration (FDA). Further, a similar sensitivity of approximately 0.9 fM concentration may be achieved for detection of food contaminants in actual orange juices, intentionally added with a trace amount of plasticizers, using the devices or optical arrangements of various embodiments containing the nanorods vertically aligned on a substrate. This suggests great potential towards real applications in food safety screening. Accordingly, the vertical Au nanorod arrays or in other words, a monolayer of vertically aligned Au nanorods, may be used as a SERS-active substrate for detection of organic chemical molecules, virus, protein, and DNA detection, even at a single-molecule level.

Further, with the tunable self-assembly of Au nanorods based on the evaporation-induced approach, self-assembly of CTAB-coated Au nanorods into vertical monolayer arrays with a sub-nm gap distance may be achieved, which may be suitable for high sensitivity, high tunability and multiplex sensing applications. Various embodiments may be based on surface-enhanced Raman scattering, which may reach single-molecular finger-printing identification. The vertical monolayer of Au nanorods of various embodiments may act as an extended nanoantenna which may generate a strong, reproducible and highly homogeneous distribution of electric fields, which may provide facile and reproducible SERS substrates that may be better than conventional substrates. Further, food contaminants such as plasticizers and melamines may be detected at a femtomolar level, which is not achievable by current technologies.

Various embodiments of the array of Au nanorods aligned vertically on a substrate may be employed for chemical sensing applications. For example, the array of Au nanorods may be used to detect any toxic chemical materials, virus and DNA in the fields of clinical test, food safety, and environmental pollution.

While the invention has been particularly shown and described with reference to specific embodiments, it should be understood by those skilled in the art that various changes in form and detail may be made therein without departing from the spirit and scope of the invention as defined by the appended claims. The scope of the invention is thus indicated by the appended claims and all changes which come within the meaning and range of equivalency of the claims are therefore intended to be embraced.

The invention claimed is:

1. A method of forming a monolayer of nanorods on a substrate, wherein the nanorods are at least substantially vertically aligned on the substrate, and wherein an edge-to-edge spacing between adjacent nanorods is equal to or less than 2 nm, the method comprising:
   providing a droplet of a solution comprising said nanorods and a surfactant on a substrate;
   controlling the temperature and the evaporation of the solution such that the internal region of the droplet is kept at near equilibrium status to allow formation of the monolayer of nanorods on the substrate, wherein each of the nanorods is coated with the surfactant; and
   removing the surfactant from each of the nanorods,
   wherein removing the surfactant comprises carrying out an ultraviolet ozone treatment on the surfactant-coated nanorods.

2. The method as claimed in claim 1, wherein controlling the temperature and the evaporation of the solution comprises exposing the solution to a temperature of between 5° C. and 25° C.

3. The method as claimed in claim 1, further comprising controlling the humidity of the environment the solution is exposed to.

4. The method as claimed in claim 3, wherein controlling the humidity of the environment comprises exposing the solution to a humidity of 60% or more.

5. The method as claimed in claim 1, wherein controlling the temperature and the evaporation of the solution comprises placing the substrate with the droplet in an enclosure.

6. The method as claimed in claim 5, wherein the substrate with the droplet are placed in the enclosure for a duration of 12 hours or more.

7. The method as claimed in claim 1, further comprising:
   forming the nanorods;
   preparing an electrolyte solution; and
   mixing the nanorods and the electrolyte solution to form the solution.

8. The method as claimed in claim 7, wherein the electrolyte solution comprises a monovalent compound.

9. The method as claimed in claim 7, wherein the electrolyte solution comprises at least one of sodium chloride, potassium chloride, potassium bromide, or sodium bromide.

10. The method as claimed in claim 7, wherein a concentration of the electrolyte solution is equal to or less than 0.03 M.

11. The method as claimed in claim 7, wherein forming the nanorods comprises:
    preparing a seed solution comprising a precursor material for the nanorods;
    preparing a growth solution comprising the precursor material; and
    mixing the seed solution and the growth solution to form the nanorods.

12. The method as claimed in claim 1, wherein the surfactant comprises hexadecyltrimethylammonium bromide or hexadecyltrimethylammonium chloride.

13. The method as claimed in claim 1, wherein each nanorod has a diameter of between 27 nm and 46 nm.

14. The method as claimed in claim 1, wherein each nanorod has a length of between 88 nm and 101 nm.

15. The method as claimed in claim 1, wherein each nanorod comprises at least one of gold or silver.

* * * * *